United States Patent [19]
Vanney et al.

[11] Patent Number: 5,843,179
[45] Date of Patent: *Dec. 1, 1998

[54] SUTURE GUARD FOR PROSTHETIC HEART VALVE

[75] Inventors: Guy P. Vanney, Blaine; Deborah A. Loch, Minneapolis; Kimberly A. Anderson, Eagan; Susan M. Mulvaney, St. Paul; Kurt D. Krueger, Stacy; Michael J. Girard, Lino Lakes, all of Minn.

[73] Assignee: St. Jude Medical, Inc., St. Paul, Minn.

[ * ] Notice: The term of this patent shall not extend beyond the expiration date of Pat. No. 5,571,175.

[21] Appl. No.: 734,360

[22] Filed: Oct. 21, 1996

Related U.S. Application Data

[63] Continuation-in-part of Ser. No. 487,497, Jun. 7, 1995, Pat. No. 5,571,175.

[51] Int. Cl.⁶ ..................................................... A61F 2/24
[52] U.S. Cl. ............................................................... 623/2
[58] Field of Search ......................... 623/2, 900; 606/148

[56] References Cited

U.S. PATENT DOCUMENTS

| | | |
|---|---|---|
| 3,546,710 | 12/1970 | Shumakov et al. . |
| 3,574,865 | 4/1971 | Hamaker . |
| 3,625,220 | 12/1971 | Engelsher . |
| 3,996,623 | 12/1976 | Kaster .......................................... 623/2 |
| 4,084,268 | 4/1978 | Ionescu et al. ............................... 623/2 |
| 4,233,690 | 11/1980 | Akins . |
| 4,276,658 | 7/1981 | Hanson et al. . |
| 4,665,906 | 5/1987 | Jervis . |
| 5,549,665 | 8/1996 | Vesely et al. ................................ 623/2 |

FOREIGN PATENT DOCUMENTS

| | | |
|---|---|---|
| 1180087 | 10/1964 | Germany . |
| WO 89/00841 | 2/1989 | WIPO ........................................ 623/2 |

*Primary Examiner*—David H. Willse
*Attorney, Agent, or Firm*—Hallie A. Finucane, Esq.; Westman, Champlin & Kelly, P.A.

[57] ABSTRACT

A heart valve prosthesis for use in a heart includes an orifice defining a lumen therethrough for blood flow. An occluder is carried in the orifice and is movable between an open position which allows blood flow through the lumen and a closed position in which flow through the lumen is blocked. A suture cuff coupled to the orifice extends around an outer circumference of the orifice and is used for attaching the heart valve to a heart tissue annulus using sutures. The sutures are knotted proximate the suture cuff to secure the cuff to the annulus. A suture guard is coupled to the suture cuff and is movable between an open position in which the suture knot is exposed and a closed position in which the suture, suture knot and suture cuff are covered.

19 Claims, 28 Drawing Sheets

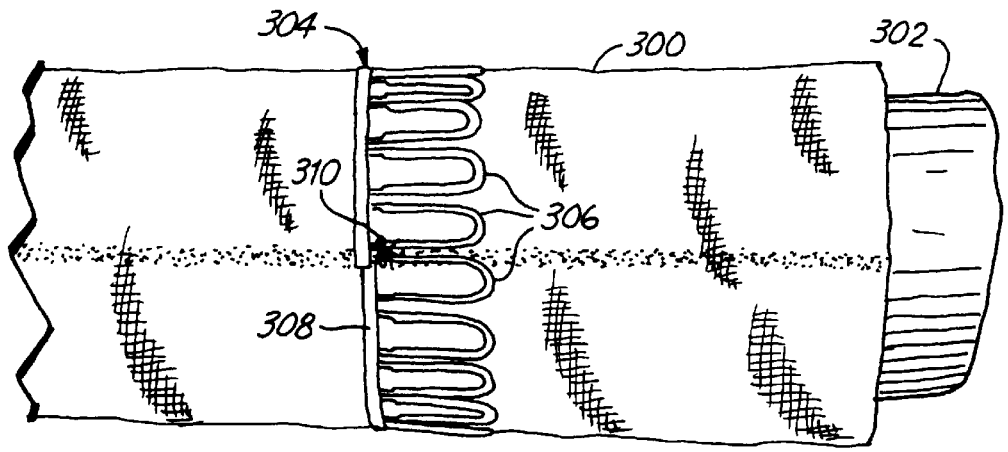
Fig. 17C
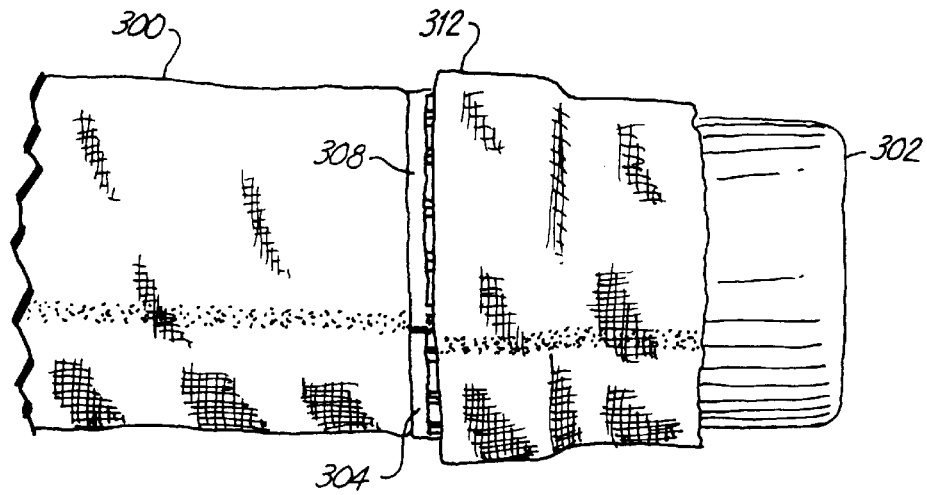
Fig. 17D1
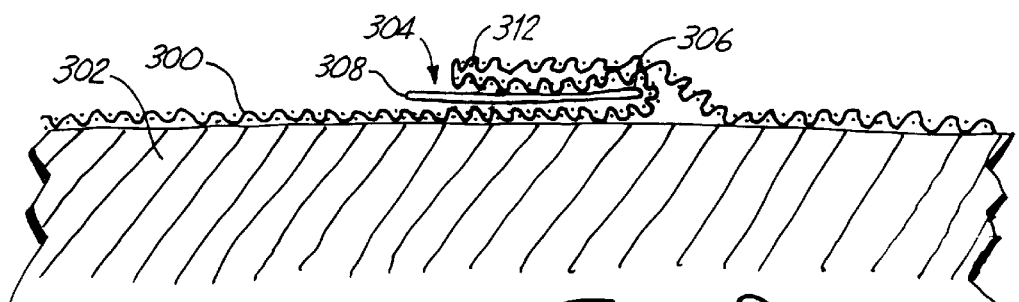
Fig. 17D2

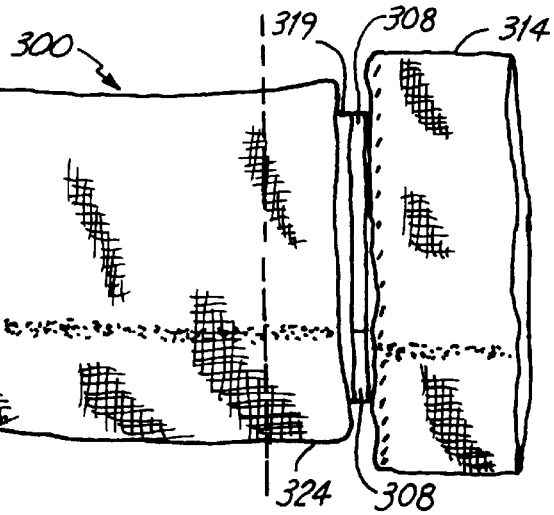
Fig. 17G
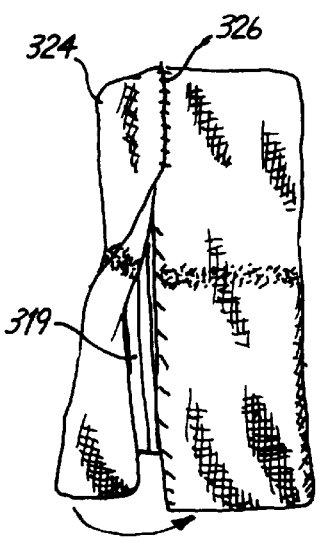
Fig. 17H1
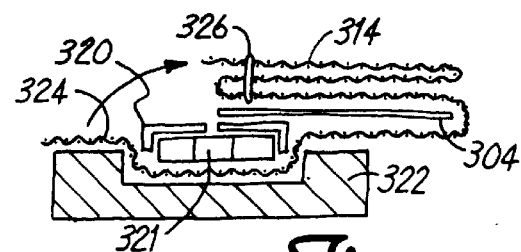
Fig. 17H2
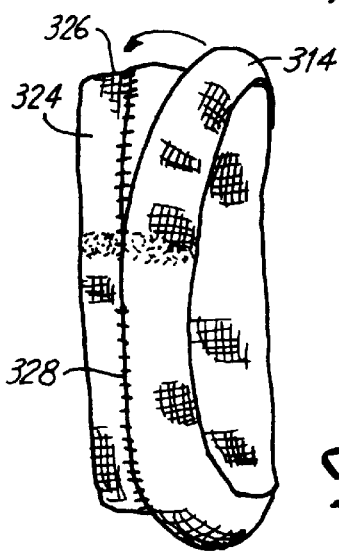
Fig. 17I1
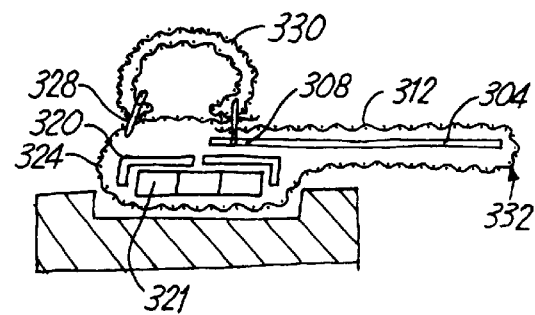
Fig. I2

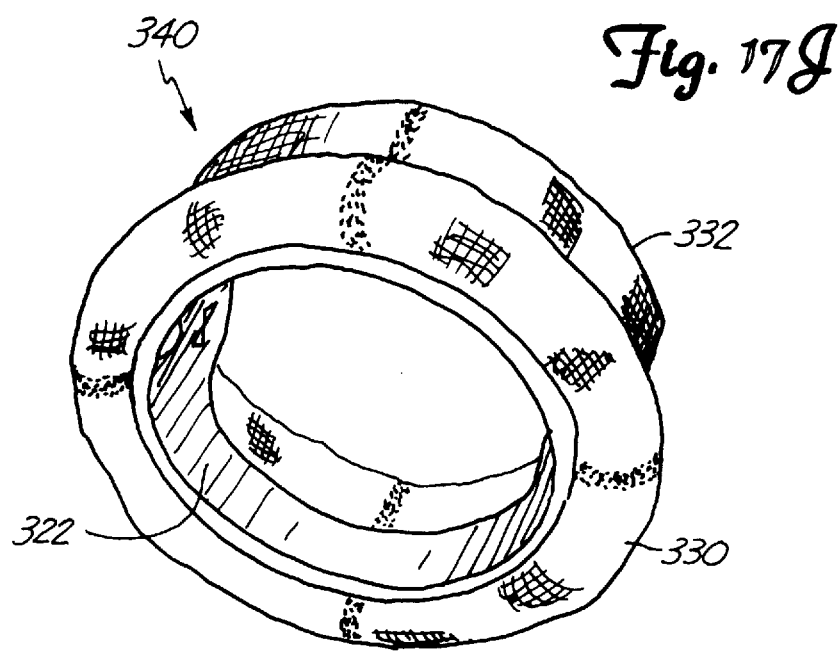

SUTURE GUARD FOR PROSTHETIC HEART VALVE

This is a Continuation-In-Part application of U.S. Ser. No. 08/487,497, filed Jun. 7, 1995, now U.S. Pat. No. 5,571,175.

FIELD OF THE INVENTION

The present invention relates to prosthetic heart valves. More specifically, the present invention relates to a shield or guard for covering a suture knot and suture cuff used with a heart valve prosthesis.

BACKGROUND OF THE INVENTION

Heart valve prostheses are used to replace natural heart valves. Prosthetic heart valves include both mechanical heart valves and tissue or bioprosthetic heart valves. In both types, a valving member is carried in an orifice body or housing. In a mechanical heart valve, the valving member typically comprises a mechanical occluder such as a leaflet movable between an open and a closed position. In a tissue valve, the valving member comprises tissue movable between an open and a closed position.

Such prosthetic heart valve prostheses require the orifice to be attached to the native heart tissue annulus left as a result of the surgical excision of the existing valve from the patient's heart. Typically, a sewing or suture cuff is attached to the valve orifice and is used by a surgeon to suture the prosthesis to the heart tissue. Such attachment requires the ends of the suture to be knotted and cut. Following attachment, the suture knots are exposed to blood flow which can cause postoperative complications, prosthesis thrombosis, thromboembolism, excessive tissue ingrowth, or interfere with operation of the valve mechanism.

The concept of covering heart tissue/valve attachment sutures is not new. The concept was described in 1964 in German Patent Application 1180087, entitled "ARTIFICIAL HEART VALVE," by Dr. Wolfgang Seidel. This publication describes a method of attaching heart valves to the native heart tissue annulus. The attachment method uses a ring, which is partially covered with fabric and has protruding "clips." The orifice and occluder are then placed within the clips. The publication mentions the benefit of covering the suture ends and suture knots to reduce thrombus and thrombo-embolic events. The publication primarily focuses on the valve attachment and the use of solid rings.

A more recent patent application, WO 89/00841, by Lillehei, Wang and Brendzel, entitled "PROTECTIVE SHIELD FOR PROSTHETIC HEART VALVES," was published in 1989. The description in this application is of a protective shield which is annular or ring-shaped to fit over a circular valve base and cover an annular sewing ring. The reference mentions methods of installing the ring and various geometries for this ring. The reference describes a separate attachment ring which is attached using sutures, friction, adhesive, a snap fit, hooks, Velcro® or conical friction.

Another patent describing sutures and suture knots is U.S. Pat. No. 3,996,623, issued Dec. 14, 1976, to Robert Kaster, entitled "METHOD OF IMPLANTING A PROSTHETIC DEVICE AND SUTURING MEMBER THEREFOR." This reference discusses a cuff configuration which has two cuff flanges. The native heart tissue annulus is captured in the space provided between the two flanges. The cuff has a flexible cured polymer core which provides resilience to the cuff flanges. The surgeon attaches the distal flange to the distal side of the native tissue with sutures and knots. The suture knots would be located on the proximal side of the tissue annulus. While the cuff/valve is being secured to the native tissue with sutures and knots, the proximal cuff is held "open." After the valve is secured, the proximal flange is released to the closed position. The cuff is secured to the orifice using heat shrink material. This method of attachment has not been readily accepted by surgeons. The current preferred method of attachment is to use a single flanged cuff which is placed on the proximal side of the native tissue annulus.

SUMMARY OF THE INVENTION

A heart valve prosthesis includes an orifice housing having a lumen formed therethrough. An occluder carried in the orifice housing is movable in the housing between an open position allowing flow through the lumen and a closed position in which flow through the lumen is blocked. A suture cuff is coupled to the orifice housing and extends around an outer circumference of the orifice housing. The suture cuff is used for attaching the heart valve prosthesis to the native heart tissue annulus left in the heart of a patient as a result of the surgical excision of the existing heart valve. A suture extends through the heart tissue annulus and the suture cuff. Opposite ends of the sutures are knotted on top of the suture cuff thereby securing the suture cuff to the heart tissue annulus. A suture guard is coupled to the suture cuff and is movable between an open position in which a suture knot is exposed, and a closed position in which the suture knot and suture cuff are covered.

BRIEF DESCRIPTION OF THE DRAWINGS

FIGS. 17A–17J show steps in accordance with manufacturing the present invention.

DETAILED DESCRIPTION OF THE PREFERRED EMBODIMENTS

A suture guard for use with a heart valve prosthesis is set forth herein which includes an additional flange integral to the proximal side of a sewing or suture cuff. This flange provides a flap of cuff material on the proximal side of the suture cuff which acts as a suture guard and allows a surgeon to cover the suture and suture knots. One suitable heart valve prosthesis is described in U.S. Pat. No. 4,276,658, entitled "HEART VALVE PROSTHESIS," assigned to St. Jude Medical, Inc., of St. Paul, Minn.

Figure 1:
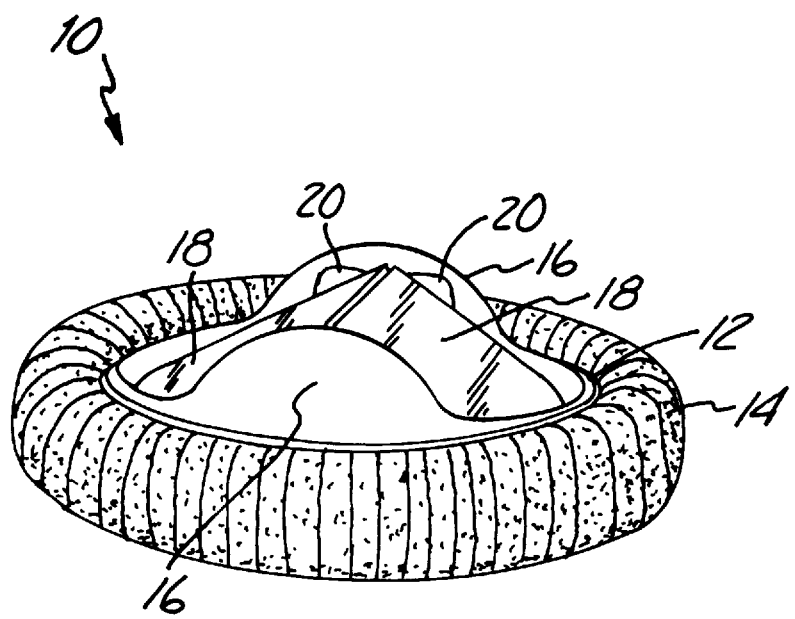
FIG. 1 is a top perspective view of a mechanical heart valve suitable for application of the suture guard techniques set forth herein.

FIG. 1 is a top perspective view of a mechanical heart valve prosthesis 10. Prosthesis 10 is shown generically and the suture guard techniques described hereinafter may be implemented on prosthesis 10, for example. Prosthesis 10 includes orifice housing or body 12. Sewing ring or suture cuff 14 extends around the outer circumference of orifice 12 and is used for attaching valve 10 to the native heart tissue annulus that remains when the existing valve of the patient is surgically excised. Orifice 12 includes pivot guards 16 which provide pivots 20 for occluder leaflets 18. A lumen is formed through orifice 12. Occluders 18 move between an open position (not shown), which allows blood flow through the lumen of orifice 12, and a closed position as shown in FIG. 1 which blocks flow therethrough.

Figure 2A:
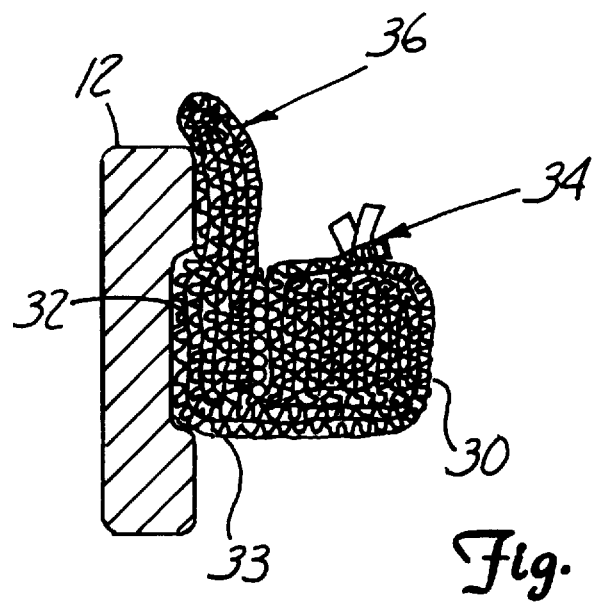
FIG. 2A is a cross-sectional view showing a suture guard in accordance with one embodiment.
Figure 2B:
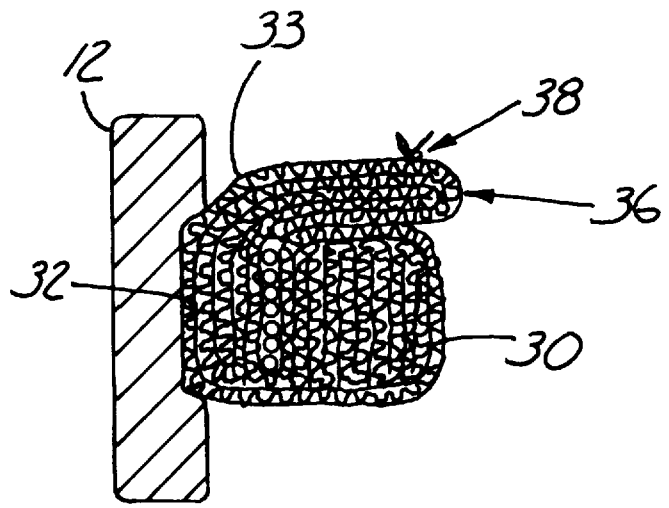
FIG. 2B is a cross-sectional view showing a suture guard in accordance with one embodiment.

FIGS. 2A and 2B are cross-sectional views of a portion of orifice 12 coupled to a suture cuff 30 carried in orifice seat 32 formed in the outer circumference of orifice 12. As used herein, suture cuffs are attached to the valve orifice using any known appropriate technique. For example, the diameter of the cuff may be reduced such that the cuff is secured in a recess which extends around the circumference of the orifice. FIG. 2A shows a suture knot 34 proximate suture cuff 30. A suture guard 36 is shown in FIG. 2A in an open position. Suture guard 36 is shown as a flap extending from an inner radius 33 of cuff 30 which is positioned over suture knot 34. Suture guard 36 is moved to the position shown in FIG. 2A during attachment of cuff 30 to the heart tissue annulus of the patient. In FIG. 2B, suture guard 36 is shown in a closed position in which guard 36 covers suture knot 34 and suture cuff 30. A small secondary suture 38 maintains suture guard 36 in the closed position. Secondary suture 38 is formed of a thinner suture material than the primary suture, and does not require the strength of the primary suture of suture knot 34 used to attach cuff 30 to the tissue annulus. Further, fewer secondary sutures 38 are required to maintain suture guard 36 in a closed position than to secure valve 10 to the tissue annulus.

Figure 3B:
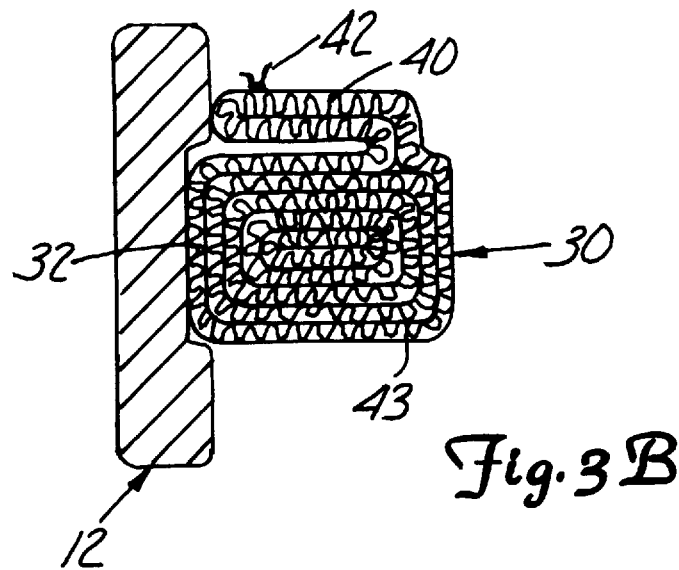
FIG. 3B is a cross-sectional view showing a suture guard in accordance with another embodiment.
Figure 3A:
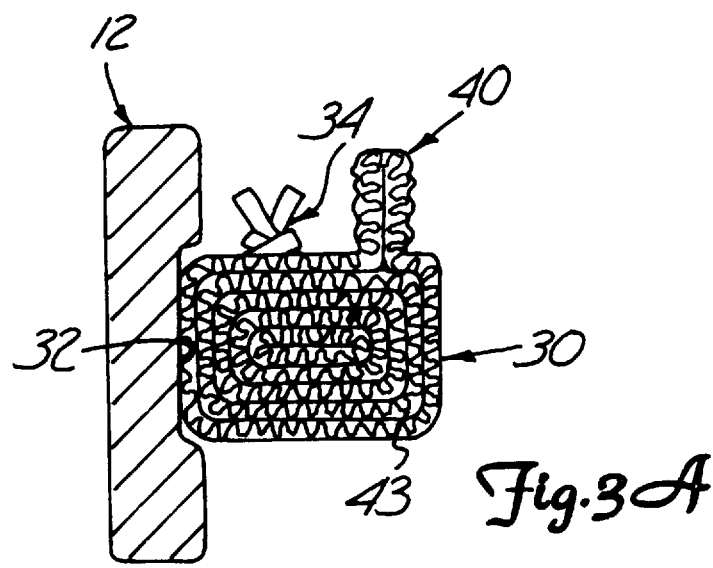
FIG. 3A is a cross-sectional view showing a suture guard in accordance with another embodiment.

FIGS. 3A and 3B show cross-sectional views of another suture guard embodiment. In FIGS. 3A and 3B, a suture guard 40 is positioned on the outer radius 43 of cuff 30 and is shown as being formed integral with cuff 30. This differs from the embodiment of FIGS. 2A and 2B in which suture guard 38 is positioned on an inner radius 33 of cuff 30. FIG. 3A shows suture guard 40 in an open position in which suture knot 34 is exposed. In FIG. 3B, suture guard 40 has been folded over to cover suture cuff 30 and suture knot 34. A smaller secondary suture knot 42 is used to maintain suture guard 40 in the closed position in FIG. 3B, similar to FIG. 2B.

In another embodiment, a biocompatible adhesive is placed between suture guard 40 of FIGS. 3A and 3B, or suture guard 36 of FIGS. 2A and 2B, and suture cuff 30. This adhesive replaces secondary suture 38 and secures guard 40 in the closed position. Typically, the suture guard is formed of a compliant material, such as woven polyester or polytetrafluoroethylene (PTFE). A biocompatible glue or fibrin glue may be used to secure the suture guard in the closed position. In this embodiment, the secondary sutures 38 and 42 may not be required.

Another alternative method for fastening the suture guard to the cuff is using hook and loop fasteners, commonly known as Velcro®. In this embodiment, the hook portion of the fastener is located on either the under side of the suture guard or the proximal side of the cuff. The loop is located on the opposite mating surface as the hook. When the suture guard is maneuvered into place so the knots are covered, the hook and loop fasteners take hold and prevent the guard from revealing the knots.

Figure 4B:
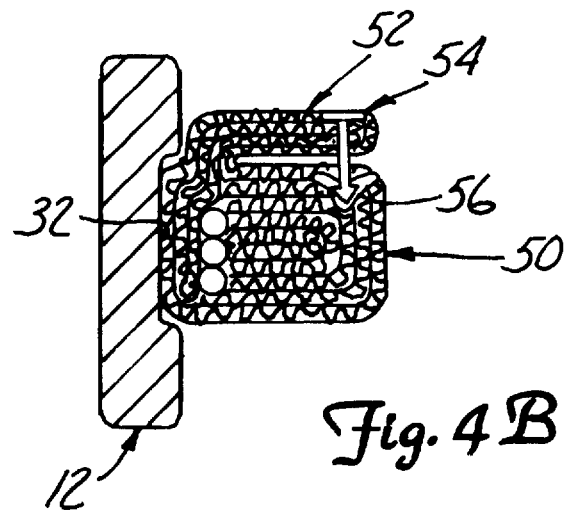
FIG. 4B is a cross-sectional view showing a suture guard in accordance with another embodiment.
Figure 4A:
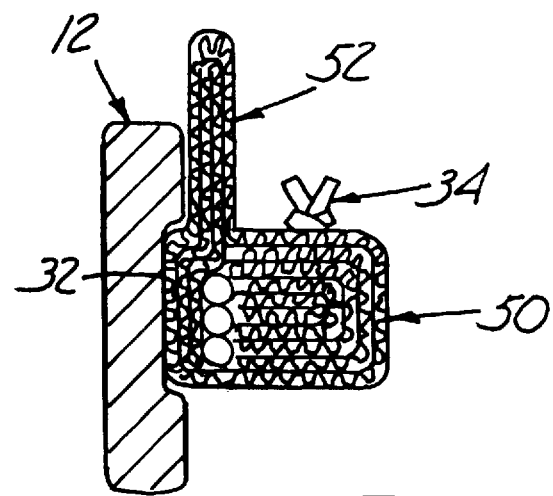
FIG. 4A is a cross-sectional view showing a suture guard in accordance with another embodiment.

FIGS. 4A and 4B show cross-sectional views of a suture guard 52 in accordance with another embodiment. Suture guard 52 is formed integral with and extends from suture cuff 50 and is folded over as shown in FIG. 4B to cover suture cuff 50 and suture knot 34. A barbed fastener 54 is placed through suture guard 52 by a surgeon and into cuff 50 as shown in FIG. 4B. Barbed fastener 54 includes a barbed point 56 which locks fastener 54 in cuff 50. Although suture guard 52 is shown as extending from an interior radius of cuff 50 in FIGS. 4A and 4B, in an alternative embodiment suture guard 52 extends from an exterior radius similar to FIGS. 3A and 3B.

Figure 5B:
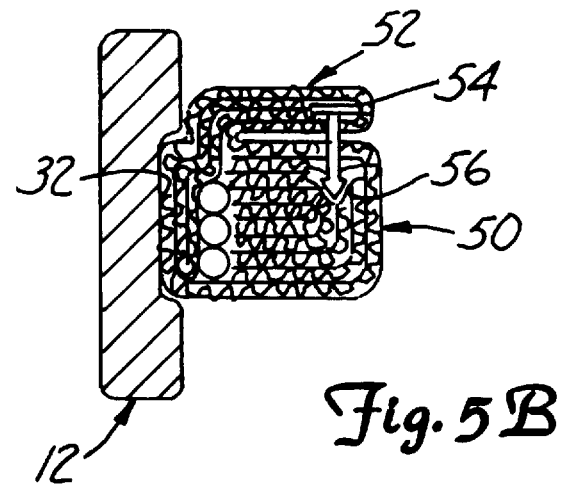
FIG. 5B is a cross-sectional view showing a suture guard in accordance with another embodiment.
Figure 5A:
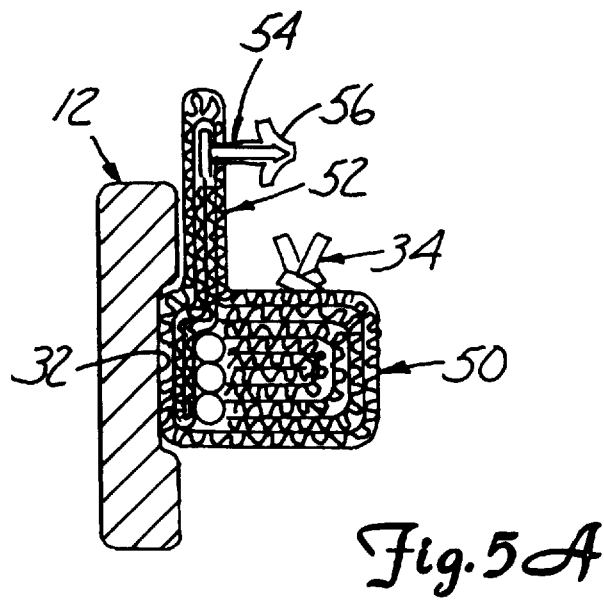
FIG. 5A is a cross-sectional view showing a suture guard in accordance with another embodiment.

FIGS. 5A and 5B are cross-sectional views which show variations on the embodiment of FIGS. 4A and 4B. In FIGS. 5A and 5B, barbed fastener 54 is embedded in the distal end of suture guard 52. The advantage of this technique is that closing of the suture guard 52 as shown in FIG. 5B is faster and easier for the surgeon, and the thrombolic complications associated with additional exposed fastener material are eliminated. Additionally, the barbed fasteners 54 are integral with suture guard 52 for an added measure of safety. Barbed fasteners 54 may be constructed as independent objects or attached to a continuous flexible ring.

One technique for maintaining the suture guard in a closed position is to spring load the suture guard. This may be particularly useful in the case of smaller aortic valves in which it may be difficult to attach the free end of the suture guard to the cuff. A spring or flexible member may be placed on the interior or exterior of the suture guard. In the relaxed position, the spring would maintain the suture guard in a closed position covering the sutures, suture knots and suture cuff without requiring any other securing mechanism. The spring can be moved into a position which exposes the proximal side of the suture cuff (i.e., an open position) allowing the suture cuff to be sutured to the heart tissue annulus by the surgeon.

Figure 6A:
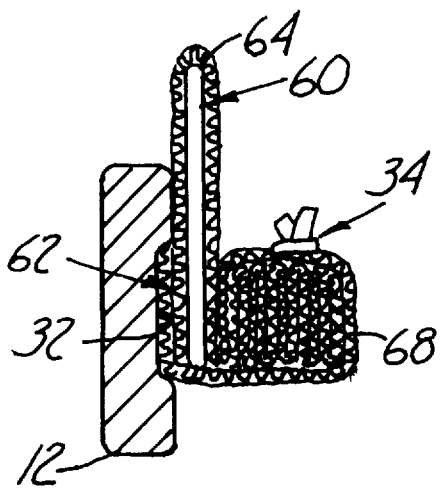
FIG. 6A is a cross-sectional view of a suture guard in accordance with another embodiment.
Figure 6B:
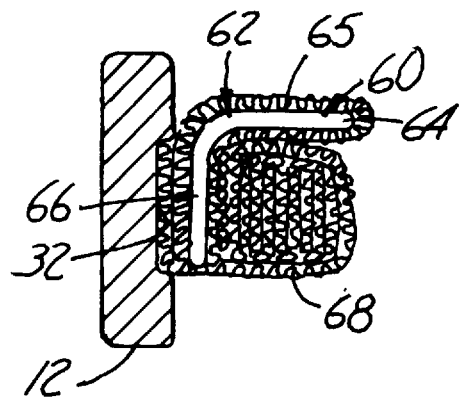
FIG. 6B is a cross-sectional view of a suture guard in accordance with another embodiment.
Figure 6C:
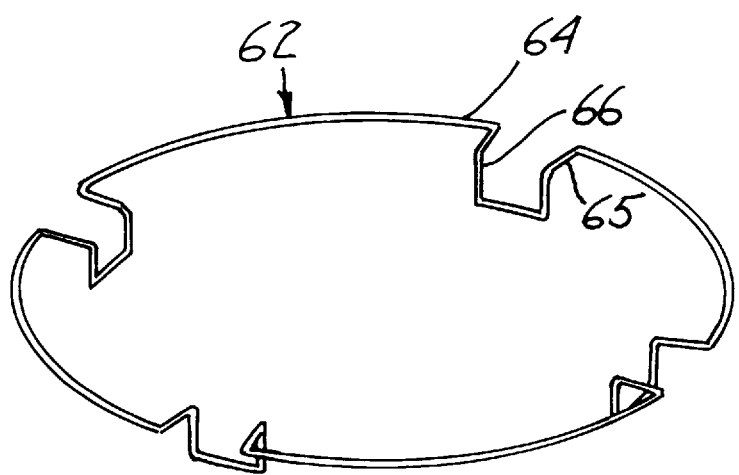
FIG. 6C is a top perspective view of a spring for use with the suture guard shown in FIGS. 6A and 6B.

FIGS. 6A and 6B show cross-sectional views of a suture guard 60 in accordance with another embodiment which utilizes a spring element 62, as shown in FIG. 6C, to maintain the suture guard 60 in a closed position. FIG. 6C is a top perspective view of wire formed spring element 62 in the closed position shown in FIG. 6B. FIGS. 6A and 6B show suture guard 60 which carries wire formed spring 62 therein as shown in FIG. 6C. Spring 62 includes circumferential portion 64, radial portion 65 and axial portion 66. Radial portion 65 extends into the suture guard 60 and is visible in the cross sections of FIGS. 6A and 6B. The axial portion 66 of spring 62 extends in an axial direction along orifice 12 and is positioned between cuff 68 and orifice seat 32 of orifice 12. Wire formed spring 62 is captured within suture guard 60, and is fixed to orifice 12 along axial portion 66. Preferable materials for wire formed spring 62 include polymers such as acetal, Elgiloy (cobalt-chrome alloy) and MP35N (cobalt-nickel alloy).

Figure 7A:
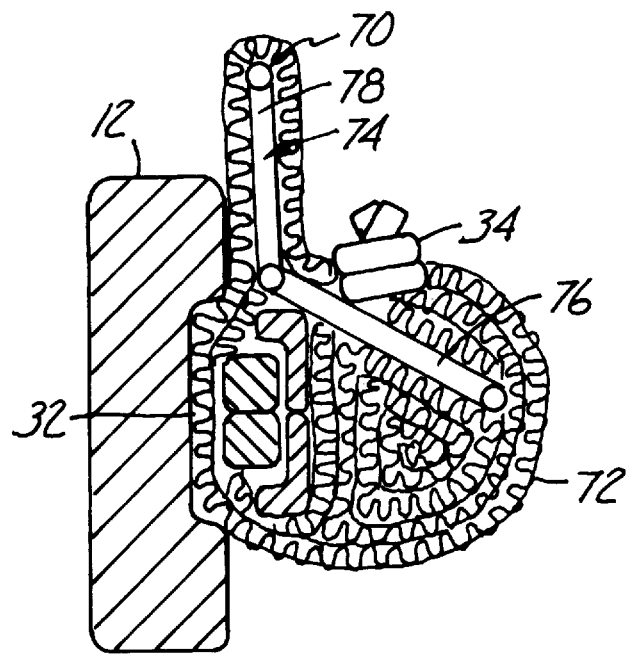
FIG. 7A is a cross-sectional view of a suture guard in accordance with another embodiment.
Figure 7B:
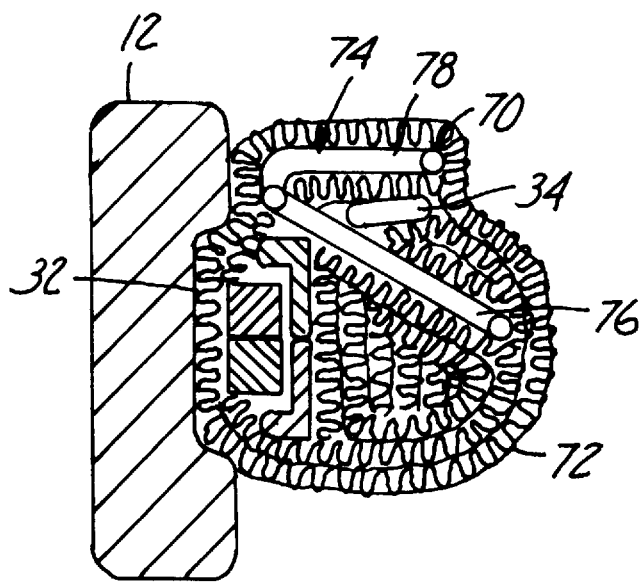
FIG. 7B is a cross-sectional view of a suture guard in accordance with another embodiment.

FIGS. 7A and 7B are cross-sectional views of a spring loaded suture guard 70 in accordance with another embodiment. In FIGS. 7A and 7B, suture guard 70 extends from cuff 72 proximate suture knot 34. An angled spring member 74 is carried in suture guard 70 and cuff 72. A lower portion 76 of spring member 74 is captured in cuff 72 while a movable portion 78 is captured in suture guard 70. Spring 70 is biased to the closed position shown in FIG. 7B. One advantage of this embodiment is that force from spring 70 is applied proximate both sides of suture knot 34 and thus tightly shields knot 34.

Figure 8A:
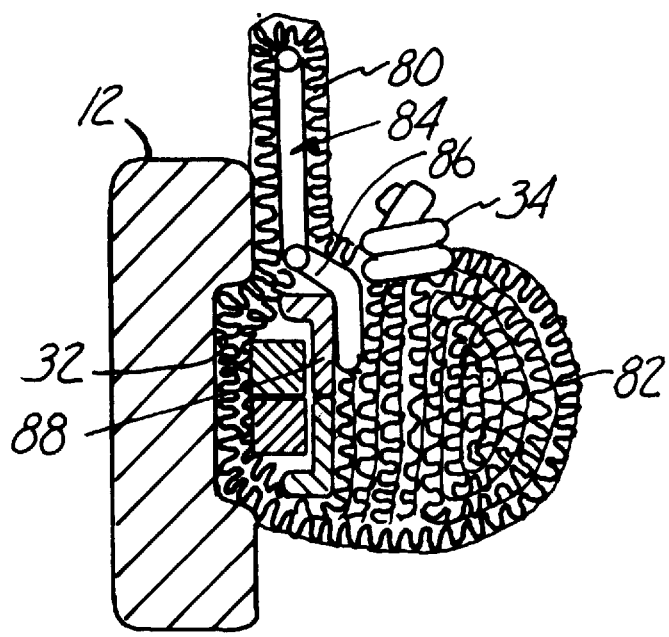
FIG. 8A is a cross-sectional view of a suture guard in accordance with another embodiment.
Figure 8B:
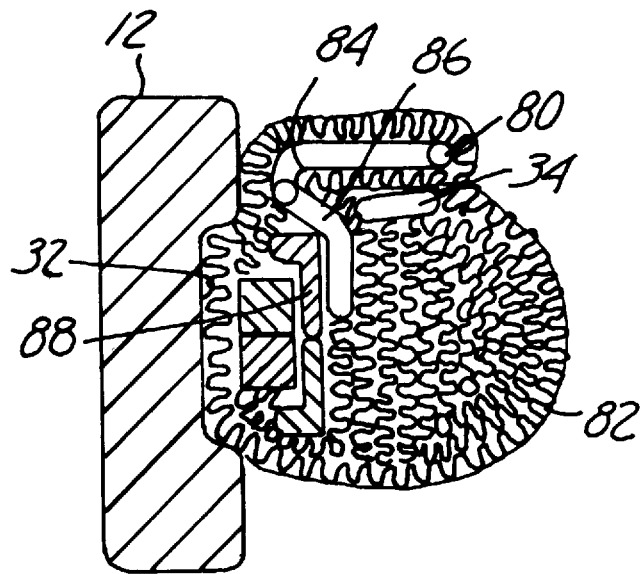
FIG. 8B is a cross-sectional view of a suture guard in accordance with another embodiment.

FIGS. 8A and 8B show cross-sectional views of a spring-loaded suture guard in accordance with another embodiment. Suture guard 80 extends from suture cuff 82 proximate suture knot 34 to cover suture knot 34 and suture cuff 82. A wire formed spring 84 is carried in guard 80 and cuff 82. FIG. 8B shows guard 80 positioned over knot 34 by spring 84. Fixed end 86 of spring 84 is attached to retaining ring 88. Retaining ring 88 secures cuff 82 in orifice seat 32 of orifice 12. Such a ring 88 may be employed in the other embodiments set forth herein. Attachment of fixed portion 86 to retaining ring 88 may be through any appropriate technique such as biocompatible adhesive bonding or welding.

Figure 9A:
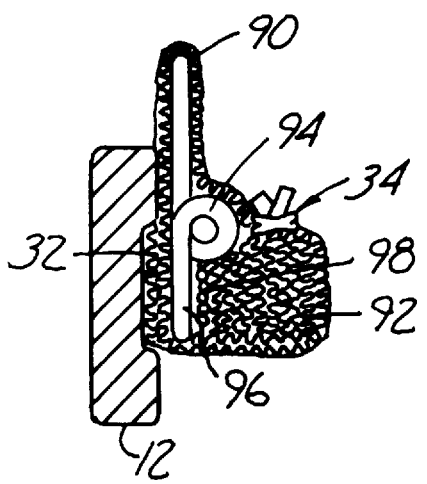
FIG. 9A is a cross-sectional view of a suture guard in accordance with another embodiment.
Figure 9B:
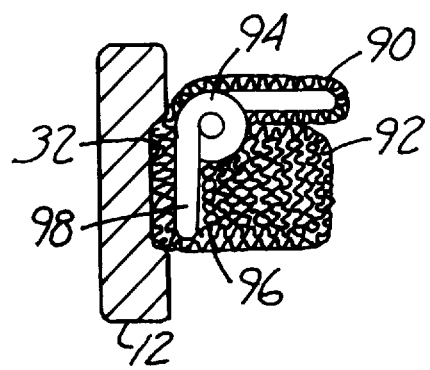
FIG. 9B is a cross-sectional view of a suture guard in accordance with another embodiment.

FIGS. 9A and 9B show cross-sectional views of a spring-loaded suture guard in accordance with another embodiment. Suture guard 90 extends from cuff 92 proximate suture knot 34. A coiled spring 94 is carried in suture guard 90 and cuff 92, and is biased to the closed position shown in FIG. 9B. A fixed end 96 of spring 94 is secured against orifice seat 32 by suture attachment windings 98. A coiled spring is advantageous because deflection of the spring member is less likely to cause permanent deformation from the original biased shape of the spring.

Figure 10:
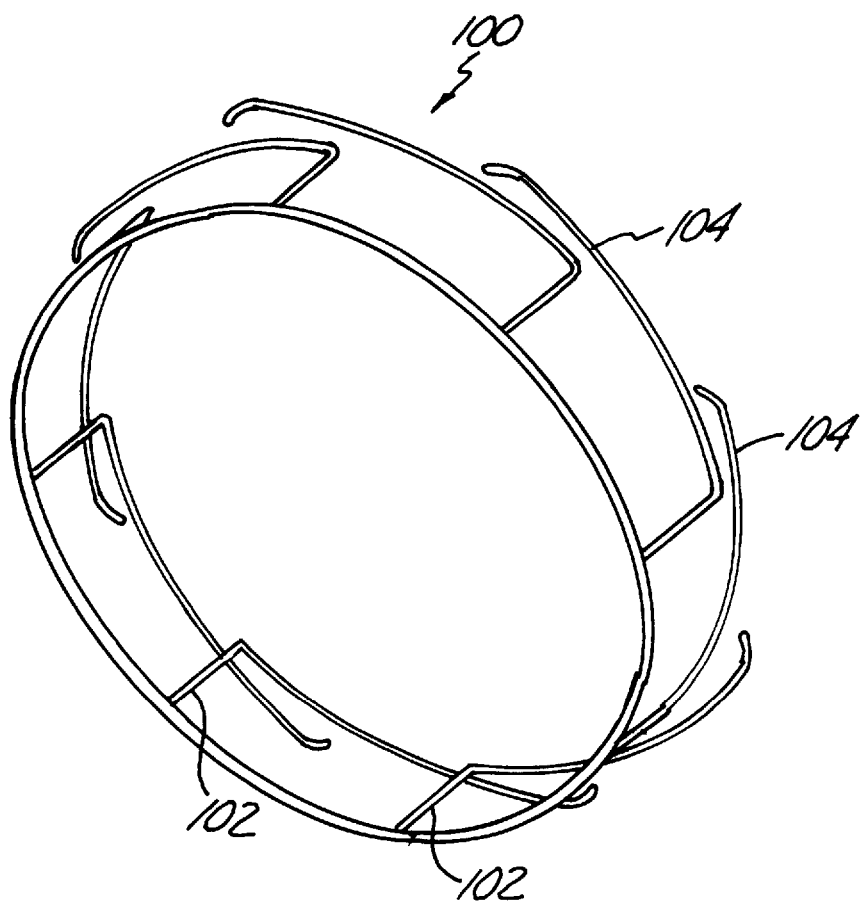
FIG. 10 is a perspective view showing a spring for retaining a suture cuff in accordance with one embodiment.

FIG. 10 is an isometric view of a spring 100 for use with a suture guard in a manner similar to that shown in FIGS. 6A through 9B. Spring 100 includes axial or fixed portions 102 which carry arms 104. Arms 104 are movable between an open position (see FIG. 6A) and a closed position (see FIG. 6B) covering the suture knot. Attachment of spring 100 to orifice 12 would occur at the fixed or axial portion 102 of spring 100.

Figure 11A:
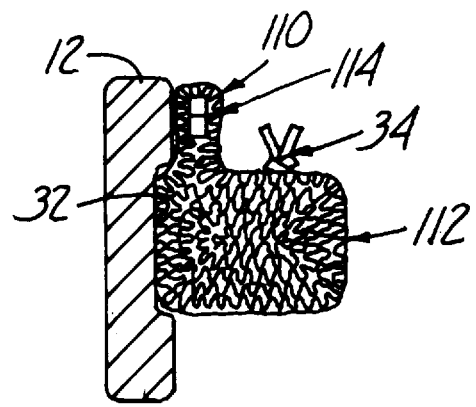
FIG. 11A is a cross-sectional view of a suture guard in accordance with another embodiment.
Figure 11B:
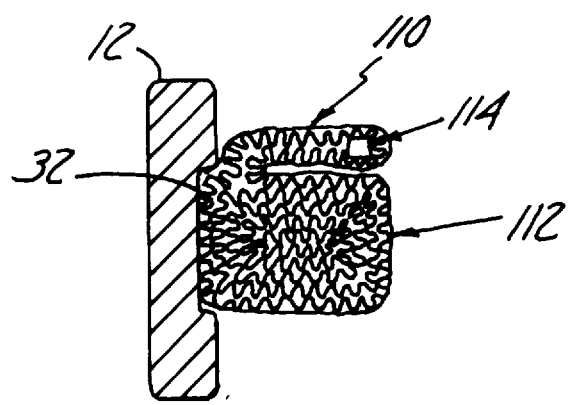
FIG. 11B is a cross-sectional view of a suture guard in accordance with another embodiment.

FIGS. 11A and 11B are cross-sectional views of suture guard 110 in accordance with another embodiment. Suture guard 110 extends from an inner radius of cuff 112 and carries spring member 114 at its distal end. Spring member 114 is an annular spring extending around an outer circumference of suture guard 110. Spring member 114 is biased to a shape which has a diameter greater than or equal to the diameter formed by suture guard 110 in the closed position of FIG. 11B. This causes suture guard 110 to be held in the closed position of FIG. 11B thereby covering suture cuff 112 and suture knot 34.

Figure 12A:
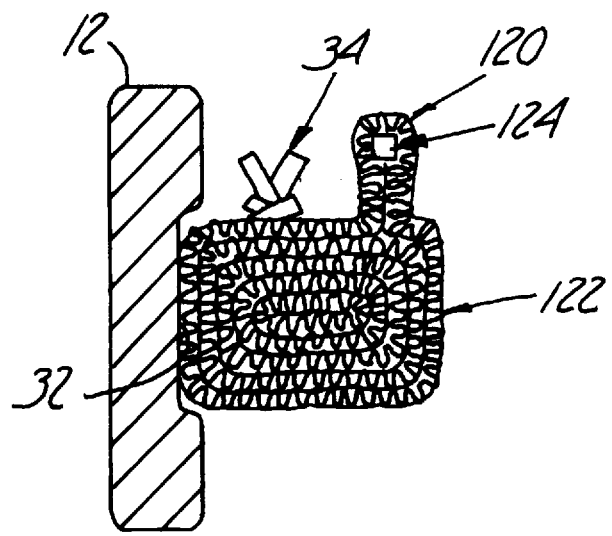
FIG. 12A is a cross-sectional view of a suture guard in accordance with another embodiment.
Figure 12B:
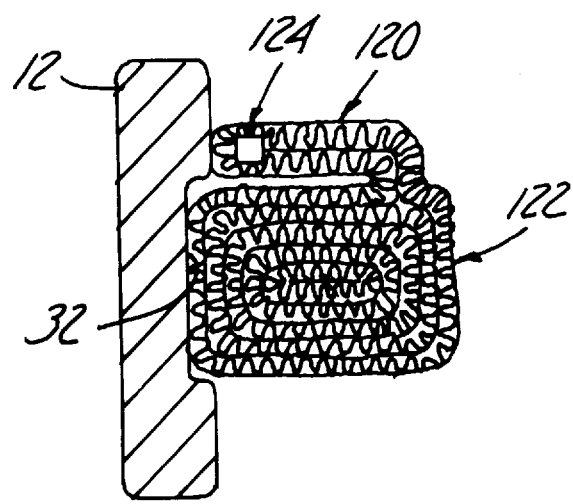
FIG. 12B is a cross-sectional view of a suture guard in accordance with another embodiment.

FIGS. 12A and 12B are cross-sectional views of suture guard 120 in accordance with another embodiment similar to the embodiment of FIGS. 11A and 11B. Suture guard 120 extends from the outer diameter of a suture cuff 122 proximate suture knot 34. The proximal end of suture guard 120 carries annular spring 124. Annular spring 124 is biased to a shape which has a diameter smaller than or equal to the outer diameter of orifice 12. This causes spring 124 to maintain suture guard 120 in the closed position shown in FIG. 12B thereby covering suture knot 34 and suture cuff 122.

Figure 13A:
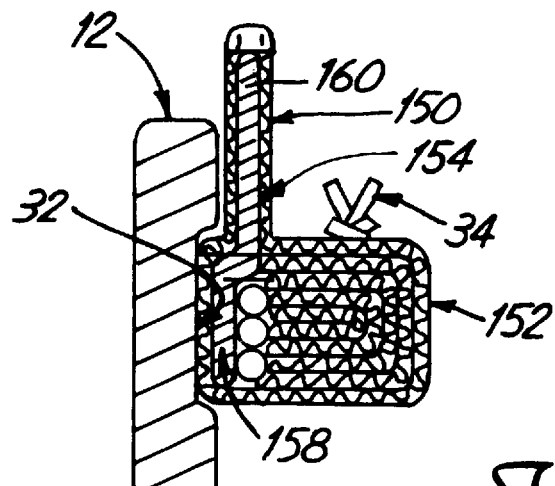
FIG. 13A is a cross-sectional view of a suture guard in accordance with another embodiment.
Figure 13B:
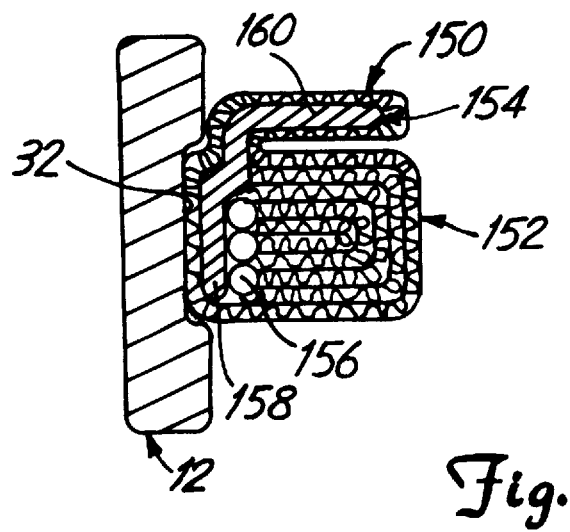
FIG. 13B is a cross-sectional view of a suture guard in accordance with another embodiment.
Figure 13C:
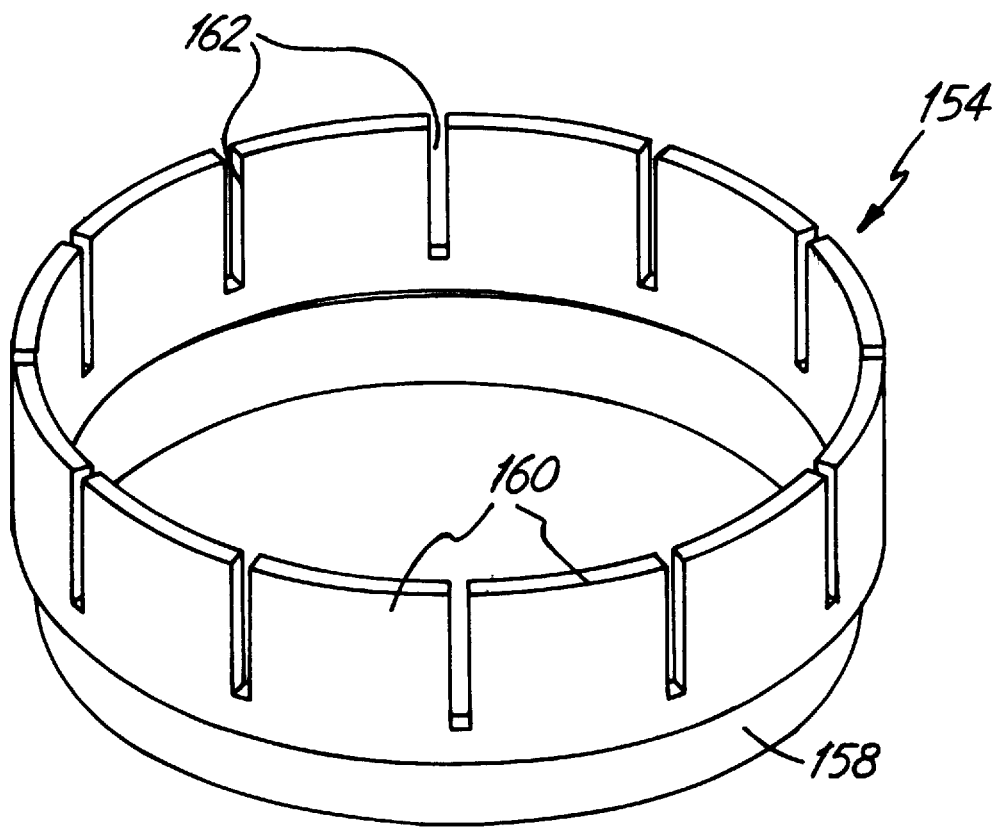
FIG. 13C is a top perspective view of a member for maintaining a suture guard in a closed position in accordance with the invention.

FIGS. 13A and 13B show cross-sectional views of suture guard 150 in accordance with another embodiment. Suture guard 150 extends from suture cuff 152 attached to orifice 12 at orifice seat 32. Spring insert 154 is carried in suture guard 150 and cuff 152. Insert 154 is secured against orifice seat 32 with suture windings 156. FIG. 13C is a top perspective view of insert 154. Insert 154 includes fixed portion 158 and movable portions 160 which is used to cover suture cuff 152 and suture knot 34. Movable portions 160 are separated by gaps 162 which allow movable portions 160 to be deflected radially outward. Insert 154 is biased to the closed position shown in FIG. 13B such that suture guard 150 covers suture knot 34.

Figure 14A:
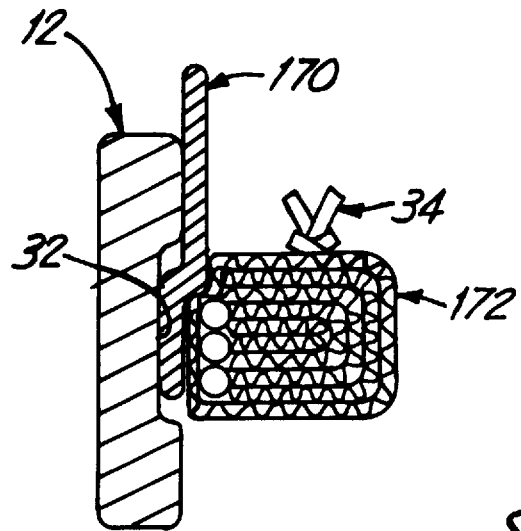
FIG. 14A is a cross-sectional view of a suture guard in accordance with another embodiment.
Figure 14B:
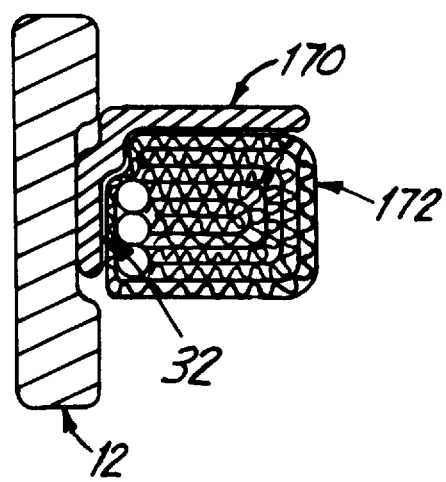
FIG. 14B is a cross-sectional view of a suture guard in accordance with another embodiment.

FIGS. 14A and 14B show another embodiment in which a spring element suture guard 170 directly covers knot 34 and suture cuff 172. Suture guard 170 may be formed similar to insert 154 shown in FIG. 13C. This embodiment may be advantageous if tissue growth is not desired or to control tissue growth. For example, guard 170 can be formed of a material which does not promote tissue ingrowth such as metals or polymers. Alternatively, guard 170 may be formed of a material which promotes controlled tissue ingrowth such as a polymer impregnated with a biologically responsive chemical. In another embodiment which is not shown, adjacent portions 160 shown in FIG. 13C overlap each other such that in the radially outward position the entire suture cuff is completely covered.

Attachment of the fixed portion of the springs set forth herein may be through any appropriate technique. For example, suture windings, retainer rings, stiffening rings or stents may be employed. The members are manufactured from biocompatible materials such as metals or polymers, for example.

In the embodiments of FIGS. 6A through 10 and 13A through 14B, the spring member can be replaced with a bendable material. As used herein, "bendable" refers to materials and constructions which substantially permanently maintain a deformation with a low degree of spring back. The initial shape of the material is in the open position. After a surgeon has fixed the valve to the heart tissue, the surgeon pushes or forms the malleable or bendable material over the suture and suture knots. This may be accomplished by either using the surgeon's finger or a tool. Further, a malleable or bendable material may be employed in the embodiments of FIGS. 6A through 9B. Suitable examples of malleable materials include polymers or metals such as tantalum or titanium.

Figure 15A:
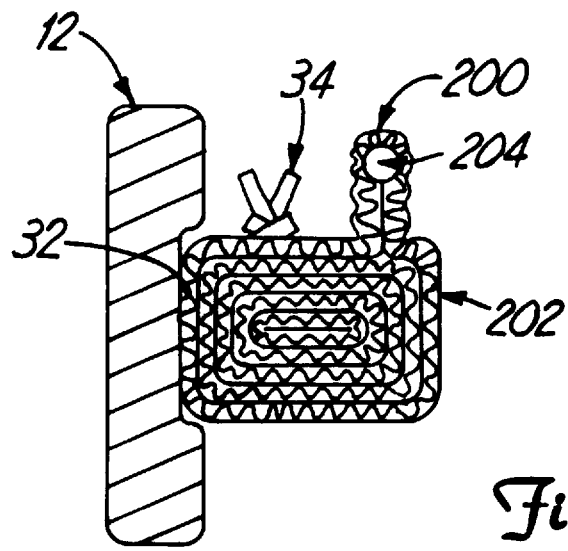
FIG. 15A is a cross-sectional view of a suture guard using a drawstring technique.
Figure 15B:
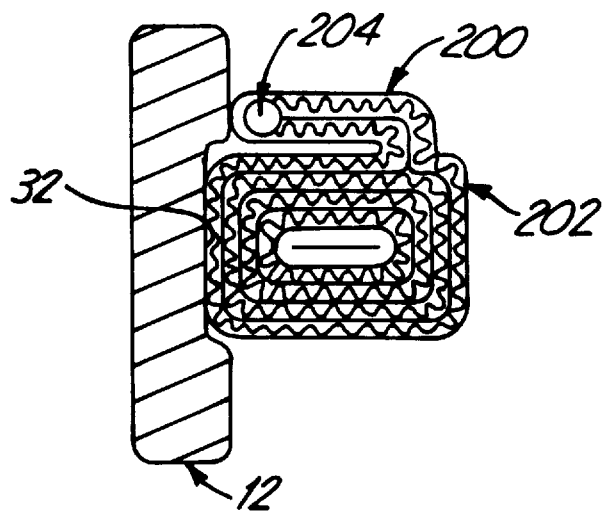
FIG. 15B is a cross-sectional view of a suture guard using a drawstring technique.
Figure 15C:
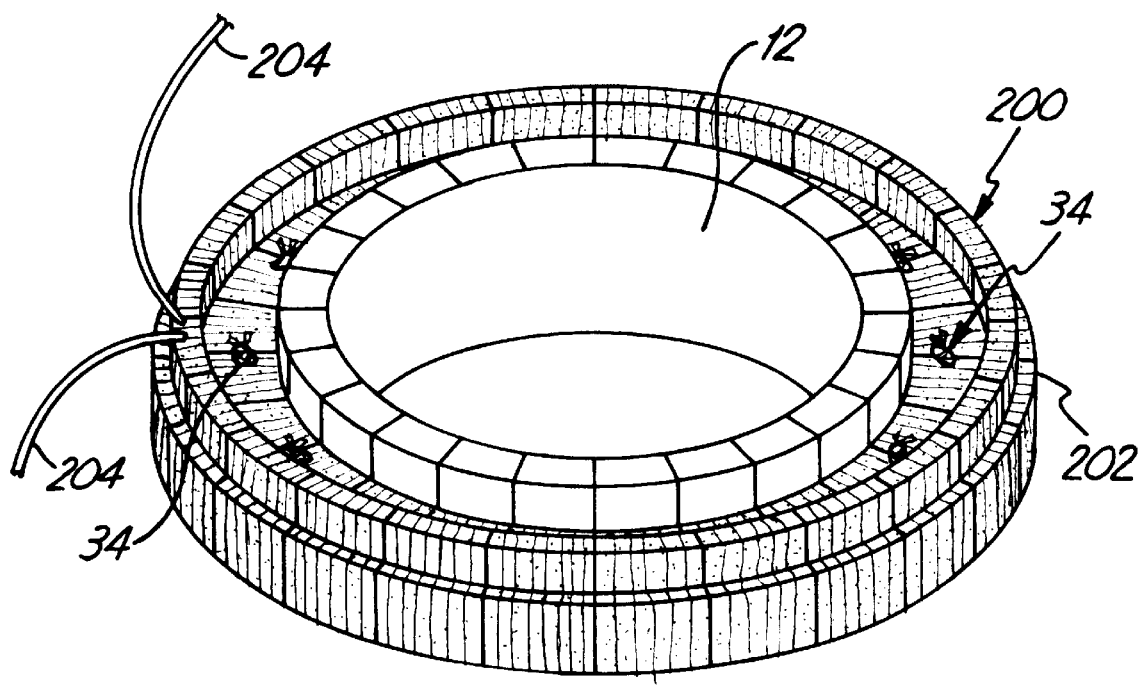
FIG. 15C is a top plan view of the suture guard of FIGS. 15A and 15B in an open position.
Figure 15D:
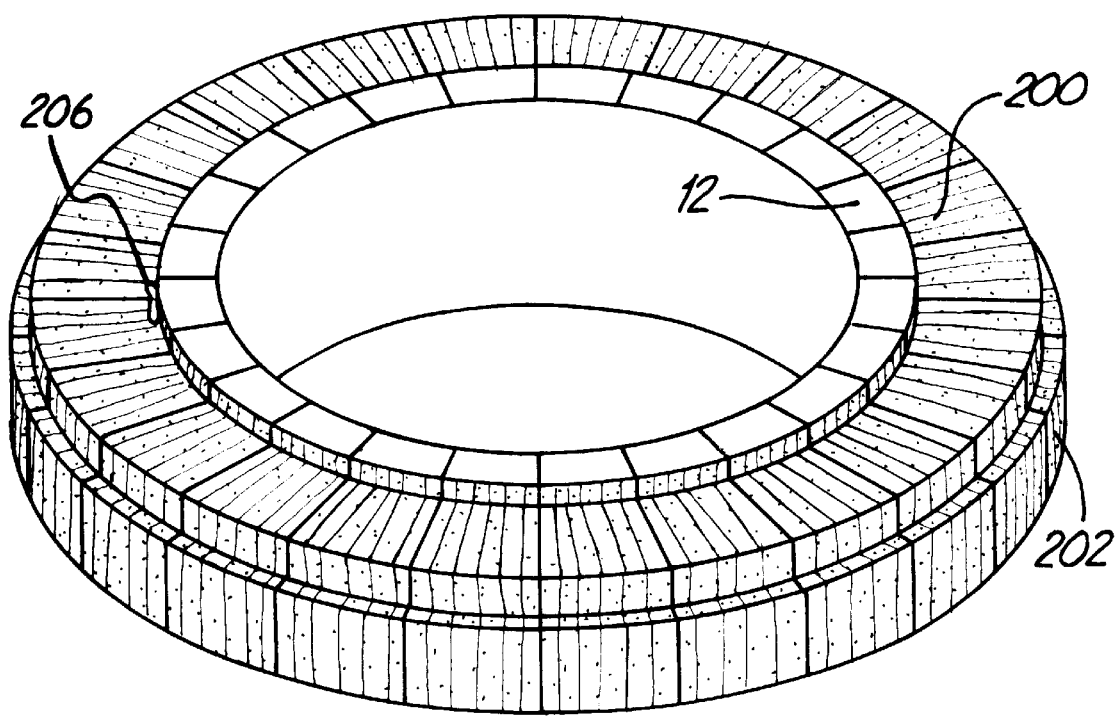
FIG. 15D is a top plan view of a suture guard of FIGS. 15A and 15B in a closed position.

The embodiments set forth in FIGS. 3 through 14 may be manufactured from materials which are temperature responsive. In these materials, a change in temperature causes the suture guard to move to the closed position. There are numerous materials which have this quality. For example, Nitinol®, and heat polymer materials such as heat-shrink polyester may be employed. Nitinol® is a nickel titanium alloy which can be deformed and which will remain in the deformed shape until heat is applied. In the present invention, the material would be deformed such that the suture guard is in the open position. After suturing is complete, the surgeon applies heat to activate the material causing the guard to assume its closed position. Application of heat by warmed cardioplegia solution causes the material to deform to its original heat-set condition. This provides a quick and easy technique for the surgeon to cover the suture and suture knots. A polyester heat shrink material which contracts radially inward to a closed position may also be employed. For example, this could be used in the embodiment shown in FIGS. 12A and 12B Another technique for restraining the suture guard is through the use of drawstring sutures. Using this techniques, sutures are placed within the proximal end, with respect to the surgeon, of the suture guard. FIGS. 15A through 15D show such a drawstring technique. FIGS. 15A and 15B are cross-sectional views showing suture guard 200 extending from the outer radius of suture cuff 202. A drawstring 204 extends through the proximal end of suture guard 200. As shown in FIG. 15B, in the closed position suture guard 200 covers knot 34. FIG. 15C is a top perspective view of suture guard 200 in the open position, as depicted in FIG. 15A. In this position, cuff 202 is exposed allowing the surgeon to form suture knots 34. After suturing is complete, the surgeon pulls drawstring 204 to move suture guard 200 to the position shown in FIG. 15D. In FIG. 15D, drawstring 204 has been tightened causing guard 200 to be pulled inward, thereby covering suture knots 34. Knot 206 is formed from drawstring 204 and may be placed under suture guard 200 thereby covering knot 206. Note that in FIGS. 15C and 15D, pivot guards and occluder leaflets have not been shown for simplicity.

Figure 16A:
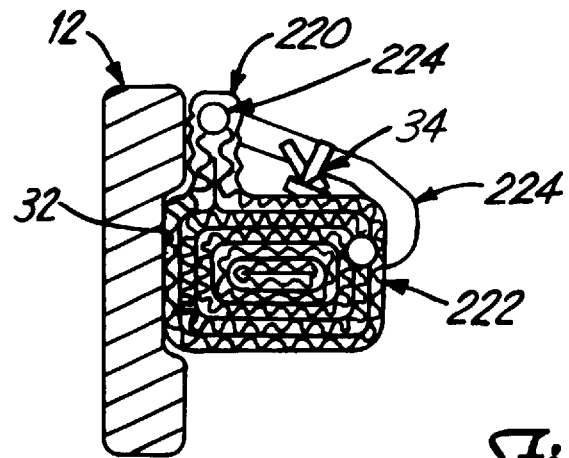
FIG. 16A is a are cross-sectional view of a suture guard using a drawstring technique.
Figure 16B:
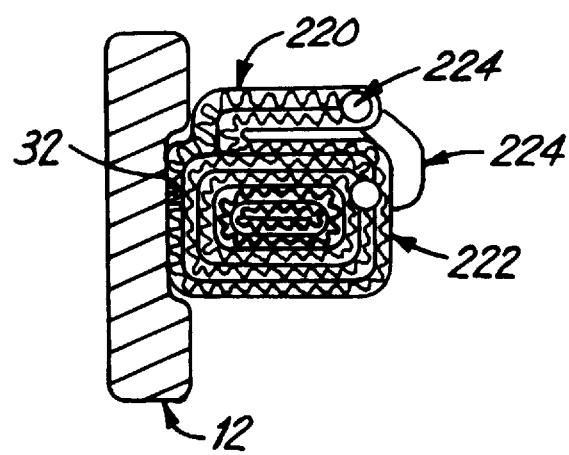
FIG. 16B is a are cross-sectional view of a suture guard using a drawstring technique.
Figure 16C:
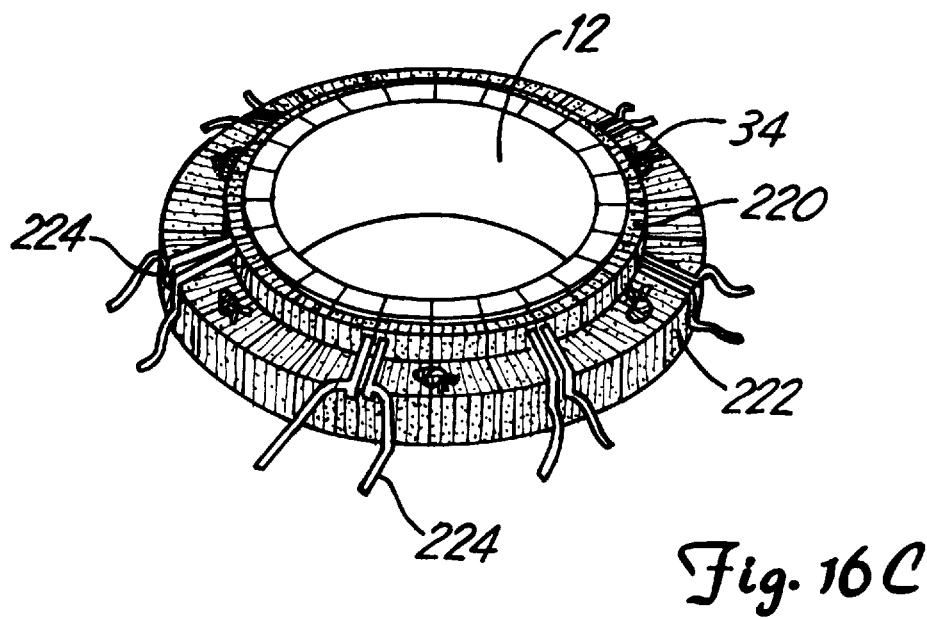
FIG. 16C is a top plan view of the suture guard of FIGS. 16A and 16B in an open position.
Figure 16D:
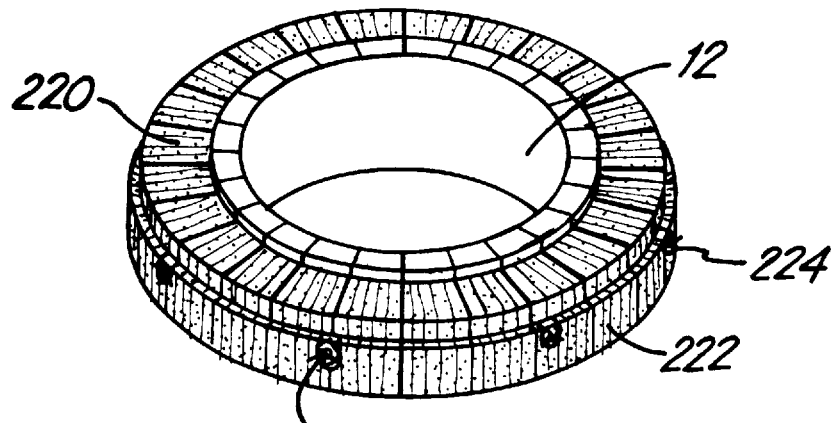
FIG. 16D is a top plan view of a suture guard of FIGS. 16A and 16B in a closed position.

FIGS. 16A through 16D show another technique using drawstrings to implement a suture guard. FIGS. 16A and 16B are cross-sectional views showing suture guard 220 extending from the inner radius of suture cuff 222. Drawstring 224 is carried through the proximal end of suture guard 220 and extends into the outer radius of suture cuff 222. As shown in FIG. 16B, drawstring 224 is tightened thereby closing suture guard 220. FIG. 16C is a top perspective view showing orifice 12 having suture guard 220 in an open position. As shown in FIG. 16C, drawstrings 224 loop through suture guard 220 and suture cuff 222. As the surgeon pulls drawstrings 224, suture guard 220 is moved to the closed position as shown in the perspective view of FIG. 16D. After cinching drawstrings 224, the drawstrings are knotted thereby securing suture guard 220 in the closed position as shown in FIG. 16D. The drawstring embodiments are advantageous because the suturing techniques are familiar and expected by surgeons.

In another embodiment, magnets may be employed in the suture cuff and suture guard to maintain the suture guard in a closed position. The suture guard set forth herein is formed of biocompatible materials.

Figure 17A:
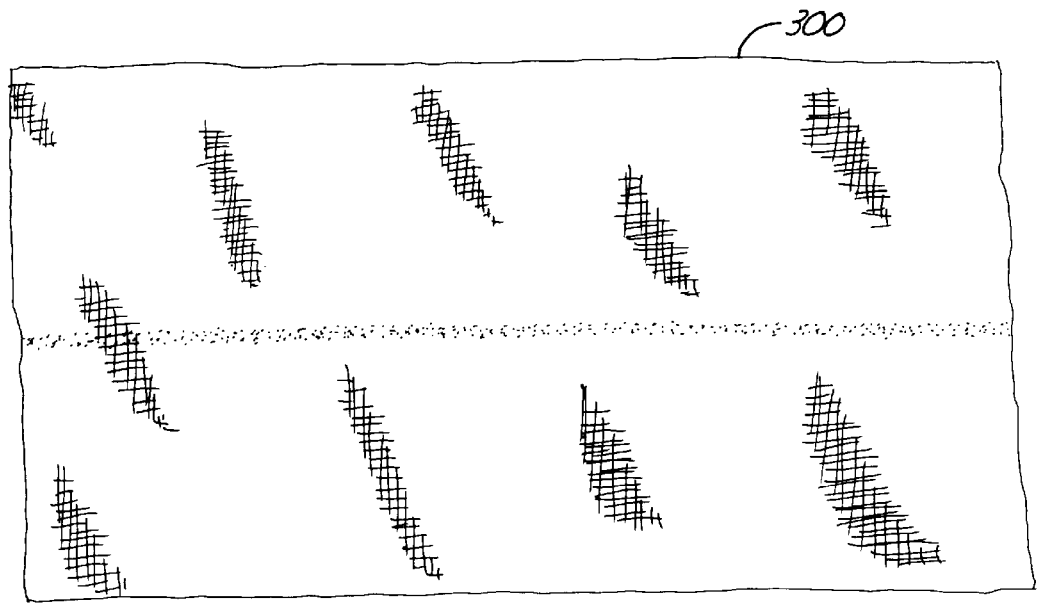
Figure 17B:
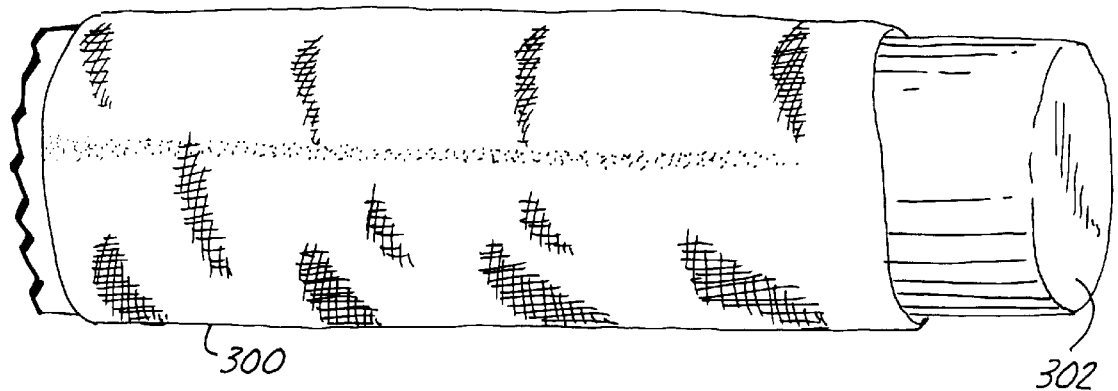

FIGS. 17A–17J show manufacturing steps in accordance with one aspect of the present invention for a heart valve prosthesis having a suture guard. As shown in FIG. 17A, an elongated tube 300 of implantable material, such as polyester fabric or polytetrafluoroethylene (PTFE) fabric, is obtained which is selected to fit over the prosthesis and carry the suture guard. As shown in FIG. 17B, tube 300 is placed over a mandrel 302. Further, the side of fabric 300 which is to be exposed following completion of the manufacturing process should be placed on the inside of tube 300 in contact with the surface of mandrel 302. As shown in FIG. 17C, a suture guard frame 304 is slid over fabric tube 300 on mandrel 302. Guard frame 304 includes a plurality of fingers 306 carried on a support ring 308. Suture guard frame 304 is formed in a circle around mandrel 302 and is sutured together at its ends by suture 310. Preferably, suture guard frame 304 is formed of a bendable material. Various embodiments of frame 304 are described below in more detail.

Figure 17F:
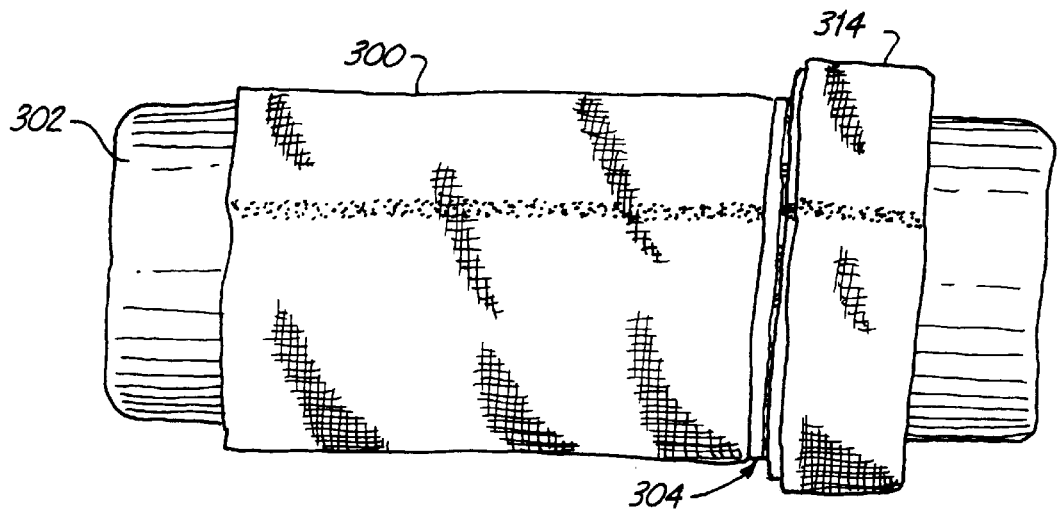
Figure 17F:
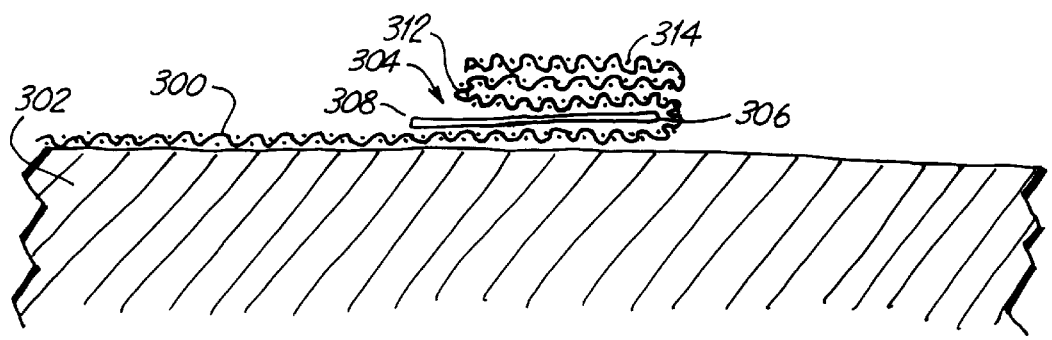
Figure 17F:
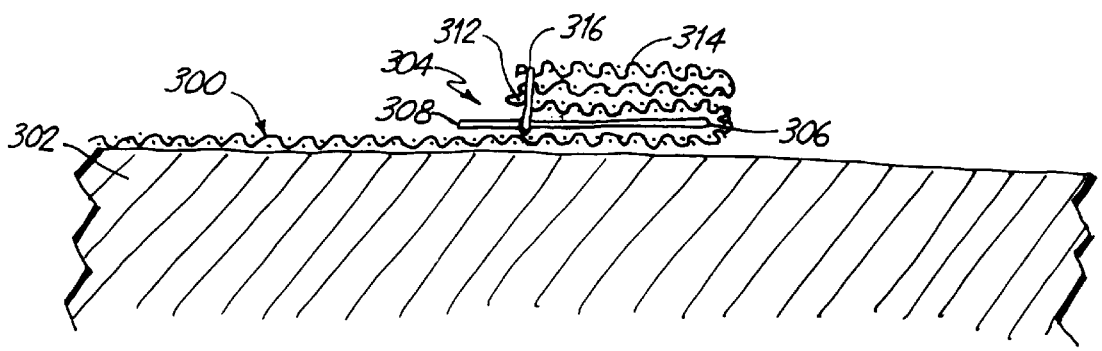

FIGS. 17D1 and 17D2 show the next step in manufacturing in which a flange portion 312 is folded partially over suture guard frame 304 while leaving support ring 308 exposed. FIG. 17D2 is a cross-sectional view showing the configuration of flange portion 312 in more detail. Next, as shown in FIG. 17E1 and 17E2, flange remainder portion 314 is folded over flange portion 312. This is shown in the cross-sectional view of FIG. 17E2 in greater detail. As shown in FIG. 17F, flange portion 312 and flange remainder portion 314 are sutured to suture guard frame 304 with suture 316.

As shown in FIG. 17G, a cuff retention mechanism 319 is placed under support ring 308 and is used to couple fabric tube 300 to prosthesis 322 shown in FIG. 17H2. A cuff retention mechanism 319, comprising retaining ring(s) 320 and springs 321, may also be configured to provide a controlled resistance to rotation such that the prosthesis may be rotated following implantation. Such a configuration is described in co-pending application Ser. No. 08/327,164 entitled "ROTATABLE CUFF ASSEMBLY FOR A HEART VALVE PROSTHESIS" which was filed on Oct. 24, 1994. The excess portion 325 of fabric tube 300 is cut along the dashed line shown in FIG. 17G. As shown in FIGS. 17H1 and 17H2, bottom flange portion 324 is folded over ring(s) 320 and springs 321 and sewn in place with suture 326. Suture 326 extends through the top layer of flange remainder portion 314.

As shown in FIGS. 17I1 and 17I2, flange remainder portion 314 is then pulled down over cuff retention mechanism 319 and sewn to bottom flange portion 324 with suture 328. This forms suture cuff 330. Further, suture guard 332 is formed by flange portion 312 which covers elongated fingers 306 of suture guard frame 304. FIG. 17J is a perspective view of the completed prosthesis 340 showing orifice body 322, suture cuff 330 and suture guard 332.

Figure 19:
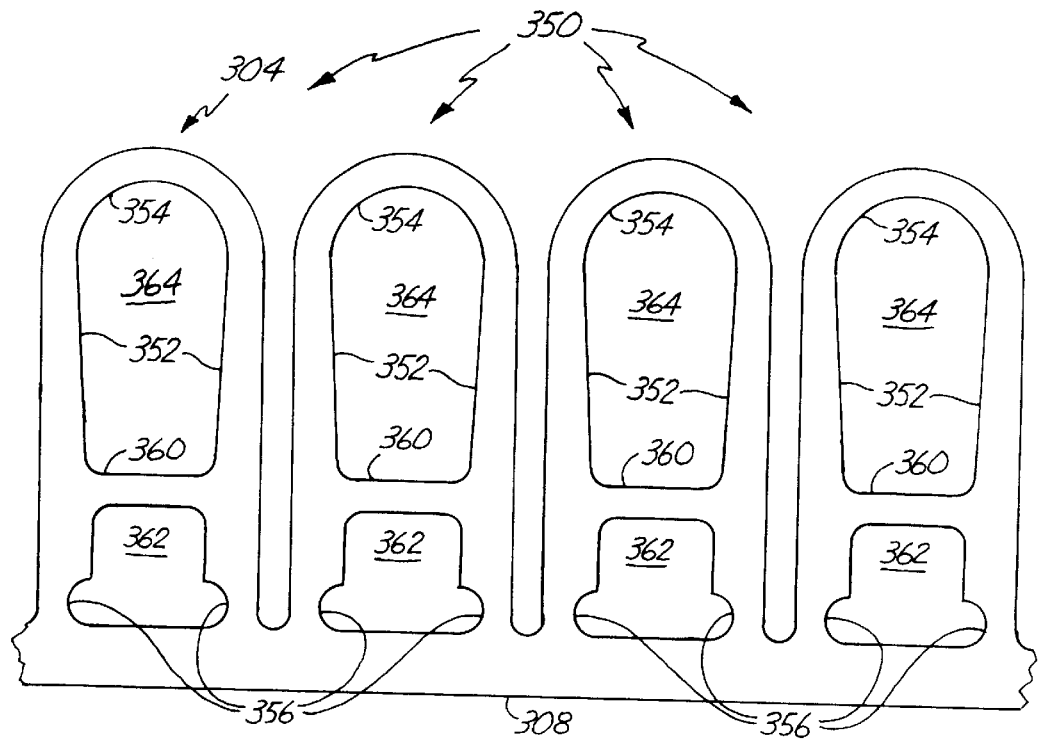
FIGS. 18–25 show plan and perspective views of a suture guard frame in accordance with various embodiments of the present invention.
Figure 18:
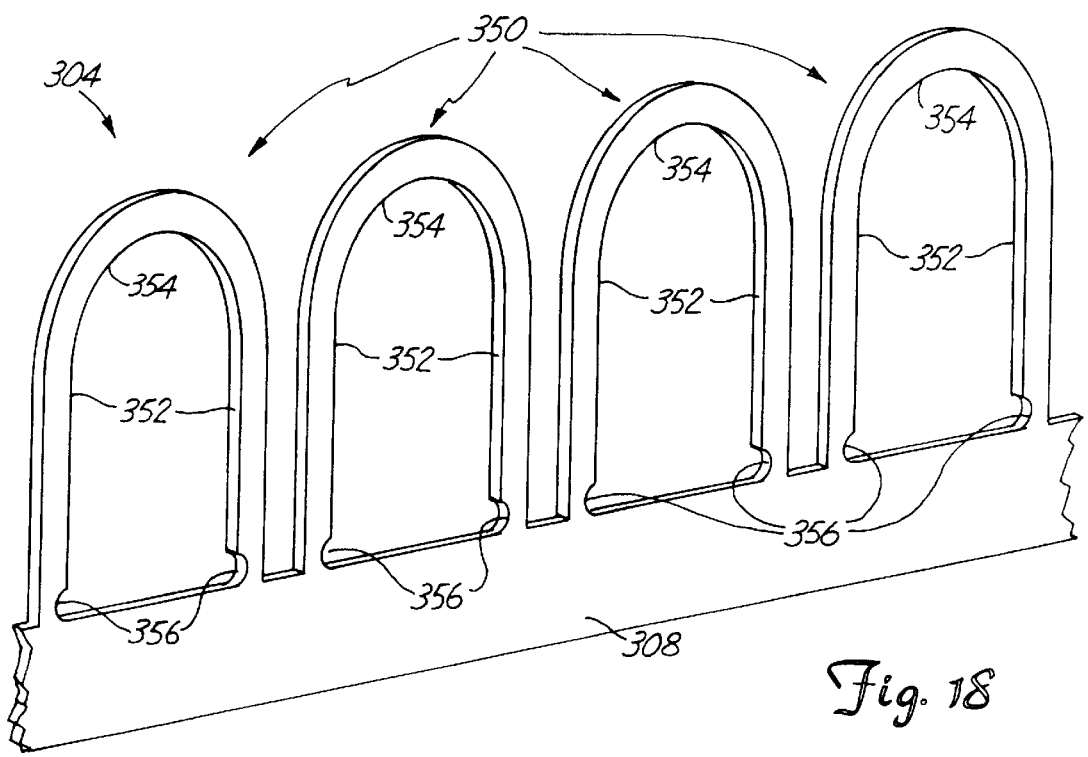
Figure 20:
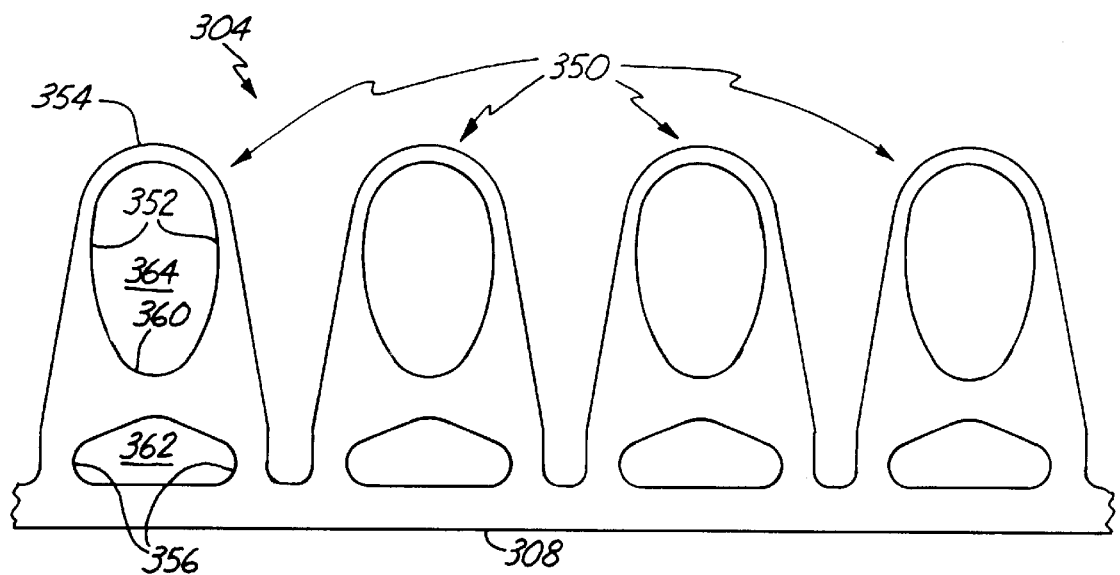

FIGS. 18–24 show various embodiments of suture guard frame 304 in accordance with the present invention. In the following description, similar features maintain their reference number for simplicity. FIG. 18 shows a perspective view of suture guard frame 304 which includes a plurality of fingers 350 which extend from support ring 308. In the embodiment of FIG. 18, each finger 350 includes two spokes 352 which support tip portions 354. An opening is defined between each pair of spokes 352 and tip portion 354. Each spoke 352 includes a region of reduced width 356 where the spoke 352 couples to support ring 308. In the embodiment of FIG. 18, tip portion 354 is concave relative to the orifice housing and provides a smooth tip such that fabric tube 300 shown in FIGS. 17A–17J is not damaged. The embodiment of FIG. 19 is similar to that of FIG. 18 and includes cross posts 360 which extend between spokes 352. In FIGS. 19 and 20, cross posts 360 inhibit bending spokes 352 in the lateral (left to right) direction. Additionally, the spokes 352 shown in FIG. 19 are wider in the region closest to the support ring 308. Cross posts 360 define a lower opening 362 and an upper opening 364 between spokes 352. FIG. 20 shows a plan view of frame 304 in accordance with another embodiment which also includes cross post 360. The shape of cross post 360 and spokes 352 may be varied to provide different shapes for lower opening 362 and upper opening 364, and thereby providing different degrees of lateral stability.

Figure 21:
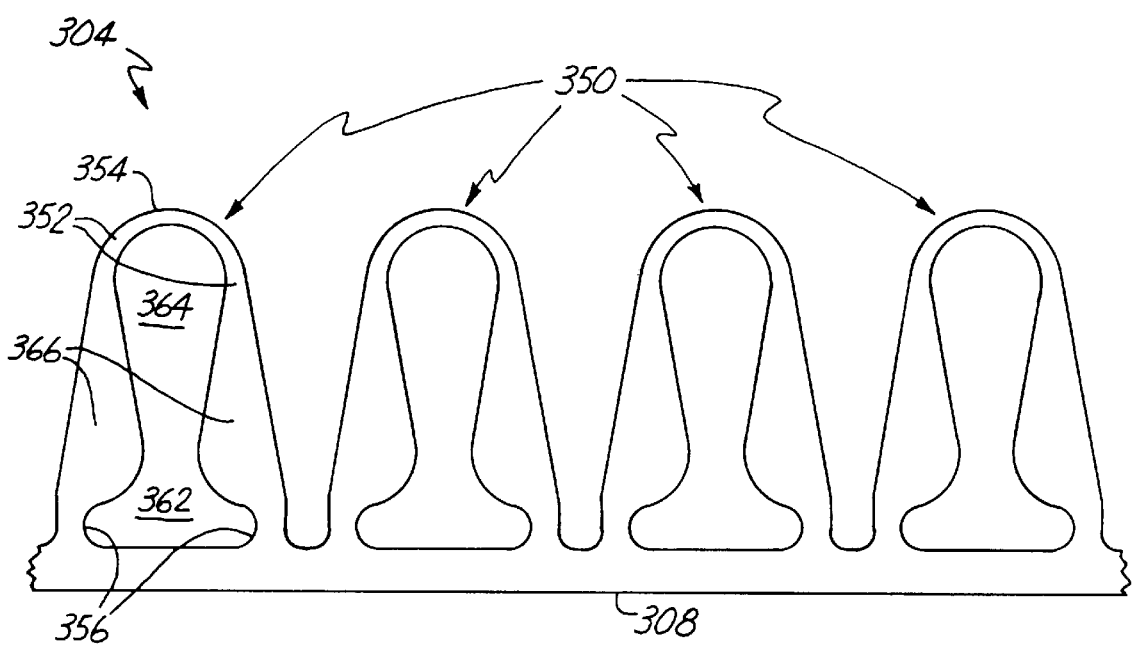
Figure 22:
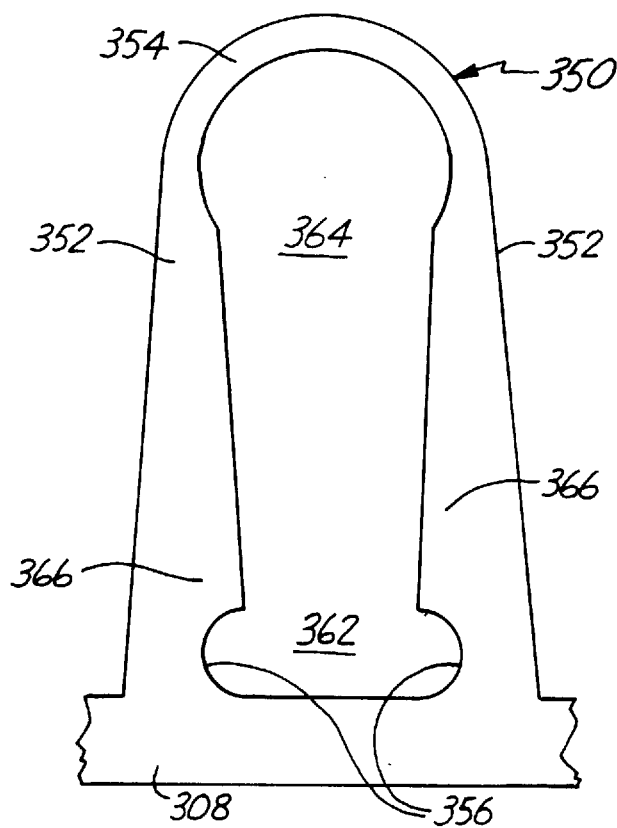

FIG. 21 is a plan view of frame 304 in accordance with another embodiment. In FIG. 21, spokes 352 include ear portions 366 which define upper and lower openings 362 and 364. The embodiment of FIG. 22 is similar to the embodiment of FIG. 21 and includes ear portions 366 having a shape different than that shown in FIG. 21 such that upper and lower openings 362 and 364 have a different shape which provide different degrees of lateral stability.

Figure 23:
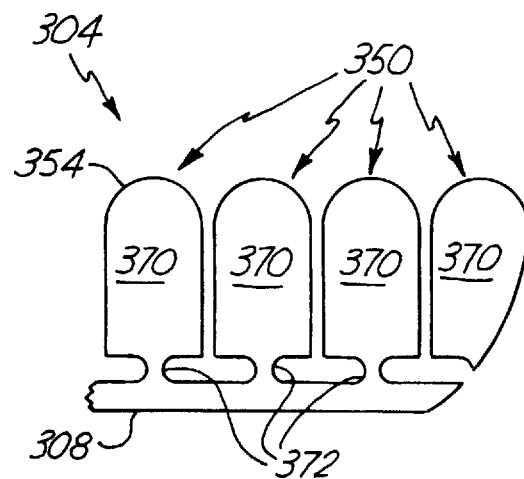
Figure 24:
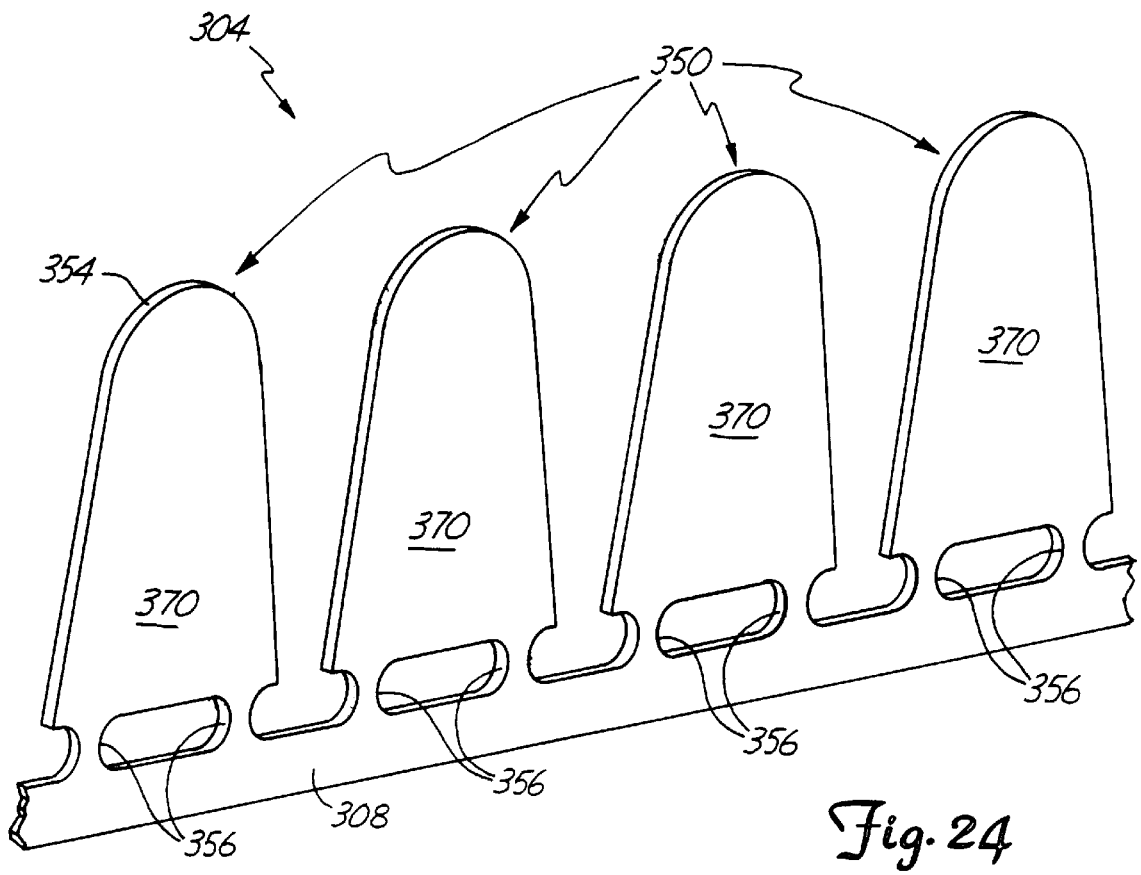
Figure 25:
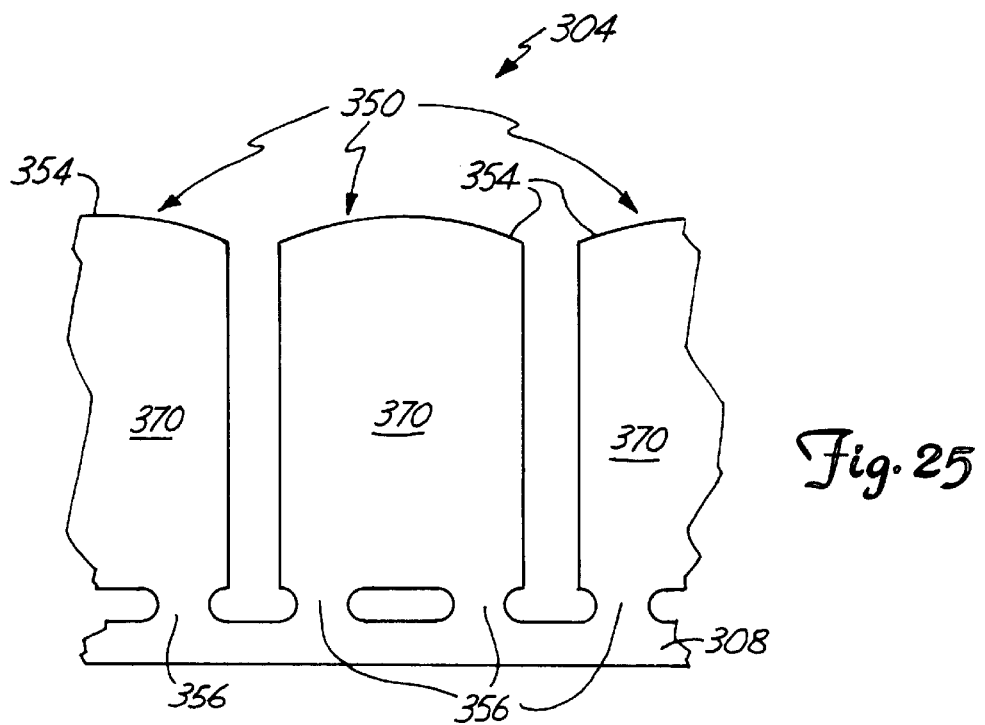

FIG. 23 is a plan view of frame 304 in accordance with another embodiment in which each elongated finger 350 includes a solid member 370 which couples to support ring 308 at a single region of reduced width 372. Tip portions 354 of each finger 350 are preferably rounded. FIG. 24 is a perspective view of frame 304 in accordance with another embodiment wherein fingers 350 include solid portions 370. In the embodiment of FIG. 24, solid portions 370 couple to support ring 308 at two regions of reduced width 356. In the embodiment of FIG. 25, tip portions 354 are somewhat square, with a slight rounding to prevent damage to the fabric 300 of the suture guard cover. This design increases the length of contact between fabric 300 of the suture guard cover and tip portions 354. This provides a smoother outer circumference of suture guard 304 when in the closed position. Generally, in this embodiment the sides of fingers 350 spread circumferentially when moved to the closed position.

Those skilled in the art will recognize that other shapes for the suture guard frame are within the scope of the present invention. These shapes include any form of elongated fingers carried on a support ring or fingers may be separably attachable to a support ring. The various suture guard frames and method of manufacture are advantageous because they are relatively easy to manufacture. Further, the suture guard frame is easily adapted for different size heart valve prostheses by cutting the guard to the appropriate length. In one embodiment, the suture guard frame is formed of tantalum such as medical grade tantalum ASTM specification F560-92 which provides excellent corrosion resistance and mechanical properties. Additionally, the suture guard frame may be used as a radiographic marker. Another advantage of the suture guard embodiments discussed herein is that they provide a relatively thin cross section and do not appreciably increase the size of the prosthetic valve. The suture guard easily conforms to variations in the tissue annulus because each of the fingers can be individually positioned to cover the annulus. The amount of force required to bend the suture guard frame can be modified by varying the material thickness and/or altering the regions of reduced width of spokes 352, including the area of reduced width 356. Additionally, this same principle can be used to control the location of bending.

The manufacturing technique is easy and inexpensive and does not require close tolerance between the individual parts. Further, the frame can be fabricated from a thin sheet of material. Preferably, the frame should be compliant, malleable or bendable enough to allow several opening and closing operations of the suture guard. The frame may be made of any biocompatible and biostable material such as tantalum. However, any biocompatible and biostable bendable material may be used such as gold, platinum, elastomers, etc. The strength of the fingers can be reduced by cutting out or removing additional material between the spokes. The stiffness of the fingers should be selected to provide sufficient rigidity to maintain the suture guard in the closed position while maintaining sufficient compliance to reduce the risk of damage to surrounding tissue. Further, the length of the suture guard should be selected such that the guard will cover the suture knots without impinging on surrounding tissue. By reducing the width of the tip region, the tip area of each finger is more compliant and less likely to damage the fabric.

The suture guard set forth herein provides a two-flange system which allows a surgeon to attach the valve using a preferred method of placing the attachment portion of the cuff on the proximal side of the native heart tissue annulus. The valve containing the suture guard can be implanted using any suturing technique such as everted mattress sutures, non-everting mattress sutures, figure of eight sutures or continuous sutures. However, the valve may be implanted using other attachment methods such as staples, rivets, or glue, and the suture guard may also be used to cover these alternative attachment mechanisms. The suture guard is formed integral with the cuff/valve assembly. The valve with the suture guard is easily manufactured and can be used by surgeons with their preferred attachment methods. The suture guard can be adapted and implemented with most existing heart valve prostheses. Some of the embodiments are self-actuated and will cover the suture knot upon release by the surgeon. The suture guard lies on the attachment portion of the cuff and tends to be flexible and therefore has the ability to conform to the irregularities commonly encountered in native heart tissue. The amount of bending and location of bending of the suture guard may also be varied and are considered to be within the scope of the invention.

Although the present invention has been described with reference to preferred embodiments, workers skilled in the art will recognize that changes may be made in form and detail without departing from the spirit and scope of the invention. For example, although the specification has discussed mechanical heart valves, the techniques set forth herein are also applicable to tissue valves (bioprostheses) and annuloplasty rings. In addition, typical materials are described in many of the preferred embodiments. However, applicable materials shall not be limited to those mentioned. Applicable material includes any biocompatible polymer, metal or other material that provides the mechanical characteristics described for the embodiments. Further, the suture guard cover may be of any appropriate material and need not be the same as the cuff material. Further still, the suture guard need not be covered, or may be covered to promote tissue ingrowth. Exposed material such as tantalum or other metal may be used to form the suture guard. Although sutures have been shown and described in the preferred embodiments, any suitable biocompatible attachment mechanism may be used.

What is claimed is:

1. A heart valve prosthesis, comprising:

an orifice housing having an exterior circumference and providing a lumen therethrough;

an occluder movable in the orifice housing between an open position allowing flow through the lumen and a closed position in which flow through the lumen is blocked;

a suture cuff extending around the exterior circumference and coupled to the orifice housing, the suture cuff adapted for receiving an attachment mechanism therethrough for attaching the prosthesis to a heart tissue annulus, wherein the cuff provides an attachment surface for carrying the attachment mechanism thereon; and a guard integral with the heart valve prosthesis which includes a plurality of elongated fingers attached to the cuff, the fingers bendable between an open position in which the attachment surface is exposed and a closed position covering the attachment surface.

2. The heart valve prosthesis of claim 1 wherein the guard includes a support ring extending around the exterior circumference of the orifice housing which carries the elongated fingers.

3. The heart valve prosthesis of claim 2 wherein the orifice housing includes first and second spaced apart rims which extend around the exterior circumference and the support ring is secured therebetween.

4. The heart valve prosthesis of claim 2 wherein the support ring is carried in the cuff.

5. The heart valve prosthesis of claim 4 wherein the cuff comprises folded cuff material.

6. The heart valve prosthesis of claim 1 wherein the cuff comprises folded fabric which covers the guard.

7. The heart valve prosthesis of claim 1 wherein at least one of the elongated fingers includes first and second spokes defining an opening therebetween.

8. The heart valve prosthesis of claim 7 wherein at least one of the elongated fingers includes a top portion which extends between the first and second spokes.

9. The heart valve prosthesis of claim 1 wherein at least one of the elongated fingers includes a tip portion which is spaced apart from the orifice housing.

10. The heart valve prosthesis of claim 9 wherein the tip portion is concave relative to the orifice housing.

11. The heart valve prosthesis of claim 1 wherein at least one of the elongated fingers includes a region of reduced width adjacent the orifice housing whereby movement of the guard between the open position and a closed position occurs substantially at the region of reduced width.

12. The heart valve prosthesis of claim 1 wherein at least one of the fingers includes a solid portion spaced apart from the orifice housing.

13. The heart valve prosthesis of claim 1 wherein the guard generally conforms to a shape of the native heart tissue annulus in the closed position.

14. The heart valve prosthesis of claim 1 wherein the fingers have a substantially constant thickness.

15. The heart valve prosthesis of claim 1 wherein the elongated fingers extend in a radially outward direction in the closed position.

16. The heart valve prosthesis of claim 1 wherein the attachment mechanism comprises a suture which forms a suture knot on the attachment surface.

17. A method of implanting a heart valve prosthesis in a heart tissue annulus of a patient's heart, comprising:

attaching a suture cuff of the prosthesis to the tissue annulus with a suture;

placing the prosthesis in the tissue annulus;

forming a knot in the suture on a knot surface of the suture cuff; and bending an attached suture guard from an open position in which the guard extends in a direction substantially parallel with an axis of the valve to a closed position in which the guard extends in a substantially radial direction and thereby covering the knot with the suture guard.

18. The method of claim 17 wherein the step of bending comprises bending the suture guard whereby the suture guard extends in a radially outward direction.

19. The method of claim 17 wherein the step of bending comprises bending the suture guard whereby the suture guard extends in a radially inward direction.

* * * * *